United States Patent [19]

Dawson

[11] 4,027,531

[45] June 7, 1977

[54] METHOD AND MACHINE FOR LOCATING VARIATIONS IN TENSION IN A SAW BLADE

[75] Inventor: Chester H. Dawson, Danbury, Conn.

[73] Assignee: Remington Arms Company, Inc., Bridgeport, Conn.

[22] Filed: Nov. 28, 1975

[21] Appl. No.: 635,962

Related U.S. Application Data

[62] Division of Ser. No. 555,155, March 4, 1975, Pat. No. 3,964,348.

[52] U.S. Cl. .................................................. 73/100
[51] Int. Cl.² .......................................... G01N 3/20
[58] Field of Search ............. 73/100, 104, 105, 144

[56] References Cited

UNITED STATES PATENTS 3,916,680  11/1975  Allen et al. .......................... 73/100

Primary Examiner—James J. Gill
Assistant Examiner—Anthony V. Ciarlante
Attorney, Agent, or Firm—John H. Lewis, Jr.; Nicholas Skovran; William L. Ericson

[57] ABSTRACT

A method and machine for hammering circular saw blades automatically, to correct uneven distributions of residual stresses, and distortions of the blade surfaces from true planes, so that the blades will run true. This operation has previously only been performed manually, by highly-skilled craftsmen. The saw blade is elastically deflected so that its normally-planar surface lies in a curved surface of a predetermined contour. A proximity sensor passes over the blade to detect deviations of its surface from the predetermined contour, which occur at points of uneven stress distribution or surface distortion. At such points, the blade is arrested and hammered until the fault is corrected.

11 Claims, 19 Drawing Figures

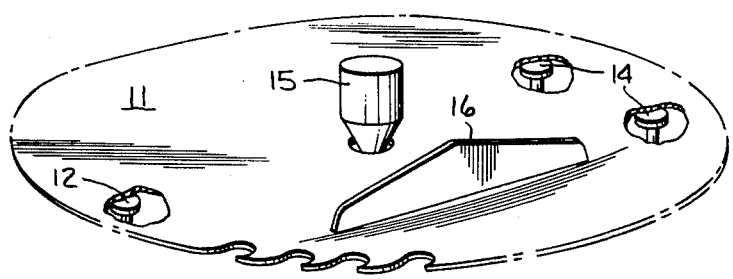
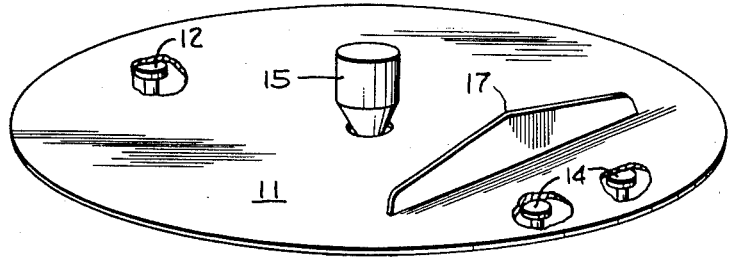
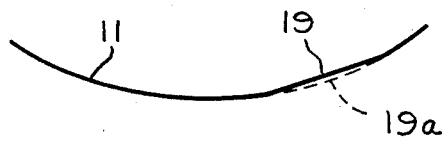
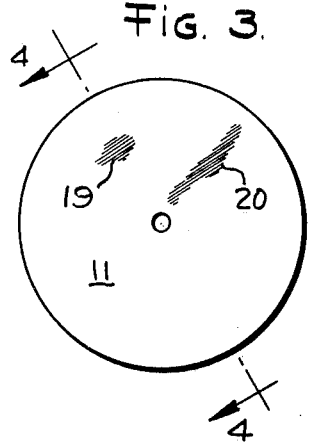
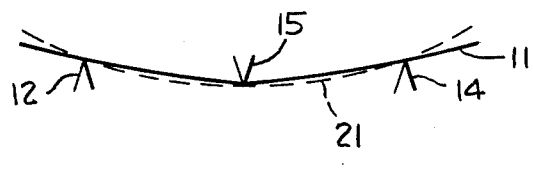
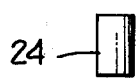
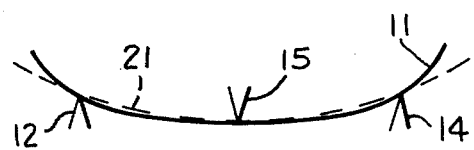
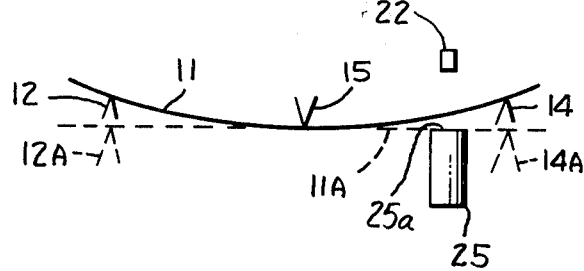

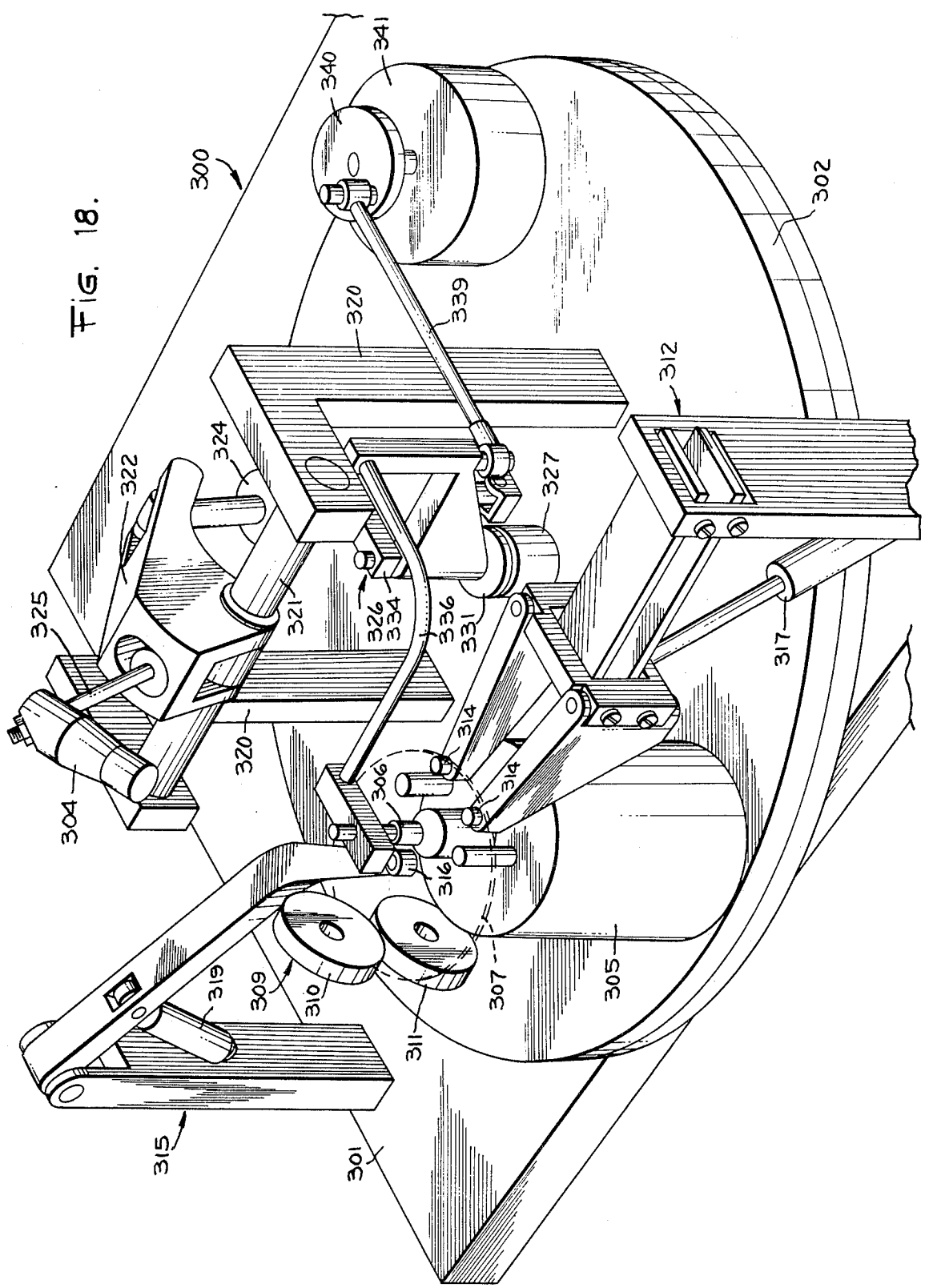

METHOD AND MACHINE FOR LOCATING VARIATIONS IN TENSION IN A SAW BLADE

This is a division, of application Ser. No. 555,155, filed Mar. 4, 1975 now Pat. No. 3,964,348.

BACKGROUND OF THE INVENTION

This invention relates to saw straightening and tensioning and, more specifically, to a novel machine and method for automatically correcting surface defects in a circular saw blade and providing the proper tension distribution to permit the blade to run straight and true at cutting speeds.

Toward the beginning of the 19th centry, the circular saw was starting to come into use, revolutionizing wood cutting methods. The speed with which the "buzz saw" was able to cut lumber was totally unheard of and unimaginable, and this new tool was generally considered miraculous. Yet in the beginning the circular saw was far inferior to modern saws in its ability to cut straight and true.

Although manufactured to the best possible tolerances, it was found that when a circular saw was operated at the high rate of rotation necessary for cutting wood, the outer edge of the saw blade had a tendency to deviate from the cutting line either to one side or the other, or to both sides, producing a somewhat wavy cut. There was also a tendency for the edge to start the cut off to one side or the other of the intended line, in which case the blade would tend to lead the cut in that direction. Yet when the saw blade was stopped, it was found to be as straight and true as before.

Eventually it was learned that the invisible defects which resulted in uneven cutting included both minute surface deformities, and improper distribution of residual tension stress in the saw. Substantial tension stress is induced in the blade by centrifugal force when it is rotated at the high angular velocities necessary for cutting wood and other materials. To this tension is added or subtracted the residual stresses in the blade, so that non-uniformity of tension distribution produces uneven strain. Irregularities in the blade surface also interfere with true running as the tension changes when cutting speed is approached. Thus the blade may be deflected from running true by either of these types of defects.

Areas on the surfaces of the blade at which residual tension stresses significantly vary from the normal level of tension in that portion of the blade are commonly referred to as "tight" or "loose" spots. Common geometric deformities include bulges, ridges, kinks and twists.

For many years, the problem of poor tension distribution and invisible surface defects was unrecognized and unsolved. The quality of a circular saw blade and its ability to cut straight and true was largely a matter of chance.

Ultimately it was learned that the operation of a circular saw could be improved by performing certain hammering operations on the saw blade. But it was found that no particular hammering method would improve the operation of all blades, and that varying types of hammering procedures must be utilized to correct different defects. The proper hammering of saws soon became recognized as a highly-skiled craft, an art requiring intuitive analysis of problems and the development of often-unique solutions. There developed a highly-skilled craftsman, the sawsmith, who has since that time been one of the highest paid representatives of all the shop trades. Because of the great skill required, the number of sawsmiths practicing this trade has remained greatly limited and the craft has often been practiced in secret, increasing the arua of mysticism surrounding this function. The sawsmith utilizes a collection of carefully-selected hammers, straight edges, and other tools, as well as senses trained by long experience, to inspect a saw blade for imperfections, mark them as to type and location, and employ the proper hammering patterns and tools to remove these imperfections from the saw. Proper hammering over both surfaces of the saw blade produces a more uniform tension distribution and removes surface flaws, enabling the saw to run straight and true at cutting speed.

While all circular saws are benefited by such hammering, omission of the procedure leaves more pronounced running defects in large circular saws than in small ones, in proportion to mass and diameter. Coupled with the high rate of pay and shortage of sawsmiths, this has dissuaded manufacturers from hammering small circular saws blades, such as those used by the home handyman. If hammered at all, they are given cursory treatment in an effort to produce a predicted tensioning. Thus, economic pressures have resulted in the marketing of inferior circular saw blades. But the cost of hammering by a sawsmith might in some cases exceed the cost of the saw itself.

In the nearly 200 years of history of the circular saw, many improvements have been made in blades and in methods for their manufacture and treatment. But after the development of the sawsmiths' craft, no further substantial advancement was made in this most difficult and expensive aspect of the treatment of circular saw blades.

The exercise of the sawsmiths' art involves "dishing" the blade, that is, elastically wraping or bending it around an axis parallel to its diameter, so that its surface takes the form of a curved cylindrical segment. The sawsmith then applies a straight edge to the blade surfaces at right angles to their curvature, which reveals to a practiced eye the nature and location of defects in the saw. Each defect is marked in a special way which points out, upon later examination, just what type each defect is, so that one may select the tools and techniques best suited for its correction. The sawsmith then places the saw on an anvil and commences hammering the marked areas, guided only by his marks, and he must be extremely careful to hammer in the proper manner and in the correct location. While this rectifying operation is being performed, the sawsmith may also hammer generally over the whole surface of the saw to obtain an overall distribution of tension appropriate to that type of blade.

When the sawsmith applies his straight edge, he is actually finding bulges and depressions representing either physical distortions, or "tight" and "loose" spots on the surface of the saw. The latter are areas of substantially greater or lesser residual tension stress than exists in the surrounding surface. When the saw is dished, any tight spots on the blade surface tend to bulge inwardly from the concave surface, being drawn out as a chord spanning a portion of this surface, while loose spots tend to bulge outwardly. When the blade is laid flat, these areas generally cannot be detected. Kinks, ridges, and other physical distortions inadvertently produced on the saw blade can also be detected by the way they stand up under the straight edge. Additionally, the manner in which the saw curves when dished is, to the skilled hand and eye of the sawsmith, a measure of overall tension distribution in the saw.

BRIEF DESCRIPTION OF THE INVENTION

The general objects of this invention are to rectify defects in saw blades without the services of skilled craftsmen; and to reduce the expense and time required for producing properly-tensioned saw blades. The invention provides a new method and an automatic machine for correcting defects in saw blades by hammering. What has been a highly-skilled, almost mystical craft may now be performed automatically by a machine and a virtually unskilled operator.

According to a preferred practice of the invention, a saw blade to be hammered is mounted on a carriage, and elastically deflected so that its surface generally coincides with a curved surface having a predetermined contour, to which the blade surface would fully conform if correctly straightened and tensioned. Preferably, the blade is deflected about an axis parallel to its diameter to lie in a curved plane, that is, a segment of a cylinder generated by a straight line moving parallel to a rectilinear axis in a curved path. Alternatively, the blade may be deflected to lie in the locus of a segment of the surface of a curved geometric solid, such as an oblate spheroid or ellipsoid, for example. The blade is caused to rotate about its center, but the deflecting means remain stationary, holding the surface of curvature of the blade in the same position; the blade flexes as it rotates to accommodate this condition.

A proximity sensor is positioned at an operating station a predetermined distance from the concave side of the curved surface of the deflected blade. A relative reciprocating or oscillating motion is created between the sensor and the carriage bearing the blade, so that the sensor sweeps through a helical path with respect to the surface of the rotating blade. The carriage may be mounted to oscillate on a pair of tilted axes, or other arrangements may be made, to cause the distance between the sensor and the locus of curvature of the surface of the blade to remain substantially constant throughout this motion.

The sensor continuously monitors its distance from the concave side of the blade surface. A tight spot, at which the residual tension is excessive, will form a chord lying inside the curve of this area. At any point where the distance to the blade surface is found to be less than the predetermined value, indicating the presence of either a tight spot or a physical deformity, the rotation of the blade and the relative motion of the carriage are immediately stopped. The sensor is withdrawn from its position over the saw blade, the blade is released from its deflected form so that it flattens out to lower the detected defective region onto an anvil, and a hammer is caused to strike this region. The hammer is then raised and the sensor returned to its operating position over the blade. After the saw has once again been deflected into its curved configuration, if the distance from the sensor to the defective area of the saw blade is found to have been corrected by the hammer blow, relative motion of the blade and carriage is resumed. If the flaw has not, however, been fully corrected, the blade and carriage remain stationary, the sensor is withdrawn, and the hammer again strikes the defect. This action continues until the defect has been corrected.

By examining and treating both surfaces of the saw blade in this way, substantially all significant defects can be swiftly and accurately repaired, eliminating the slow, laborious examination, marking of defects, and hammering which previously had to be performed manually by an expert sawsmith.

It will be observed from the foregoing that the principle on which this invention operates is that defects in a saw blade surface can be detected by locating local displacements from a predetermined curved surface into which the blade is elastically warped, or by detecting local variations in the distance from a parallel curved surface uniformly spaced away from the predetermined surface. The features of the improved method may be summarized, and contrasted with previously-known methods, by the following:

1. As opposed to bending the blade with a random degree of curvature, I bend it into a predetermined, predictably-curved surface.

2. In place of bending the blade about only one axis, or at most several axes, I rotate it continuously while retaining the surface of its curvature in a fixed location, thereby subjecting the body of the blade and any defective areas to flexure successively about every diameter. This improves the reliability of discovery of defects, many of which may be asymmetrical and therefore show up more prominently when bent about one diametral axis than another.

3. Instead of detecting defects by placing a straight edge parallel to the axis of curvature in an attempt to identify at one time all deviations from rectilinearity along the full length of a chord of the blade surface, I employ a sensor which individually checks only a small surface area at a time, thus avoiding the introduction of ambiguity by the mutual interplay of various defects in a large-area sample.

4. As opposed to marking the discovered defects in a separate operation and hammering them later, I obviate the need for the marking step by halting and relaxing the blade immediately upon detecting each defect, and correct it by hammering then and there.

5. Instead of undertaking to correct saw blades by a purely-manual guesswork method, I perform the detection and correction operations with much more reliable, as well as more rapid, automatic or semiautomatic means. Where such low production rates are desired that the cost of an automatic machine is not justified, by method may be performed with the use of at least partially manually-operated equipment conforming to the invention, with an improvement in the uniformity of resutls, and with comparatively-unskilled labor.

DESCRIPTION OF THE DRAWINGS

While the specification concludes with claims particularly pointing out the subject matter which I regard as my invention, it is believed that a clearer understanding may be gained from the following description of preferred embodiments thereof, referring to the accompanying drawings, in which:

FIG. 1 is a diagrammatic isometric view of a deflected circular saw blade;

FIG. 2 is a diagrammatic perspective view showing the deflected saw blade of FIG. 1 turned through an angle of 90°;

FIG. 3 is a plan view of a circular saw blade, showing exggerated surface defects marked thereon;

FIG. 4 is a diagrammatic cross-sectional view taken substantially along the line 4—4 of FIG. 3, illustrating the behavior of a surface defect of a deflected saw blade;

FIGS. 5 and 6 are diagrammatic cross-sectional views of circular saw blades, illustrating the effects of overall tension distribution;

FIG. 7 is a schematic view generally illustrating the operation of the straightening and tensioning machine of this invention;

FIG. 18 is a view in perspective of an alternative embodiment of the straightening and tensioning machine of this invention.

THE METHOD

Figure 8:
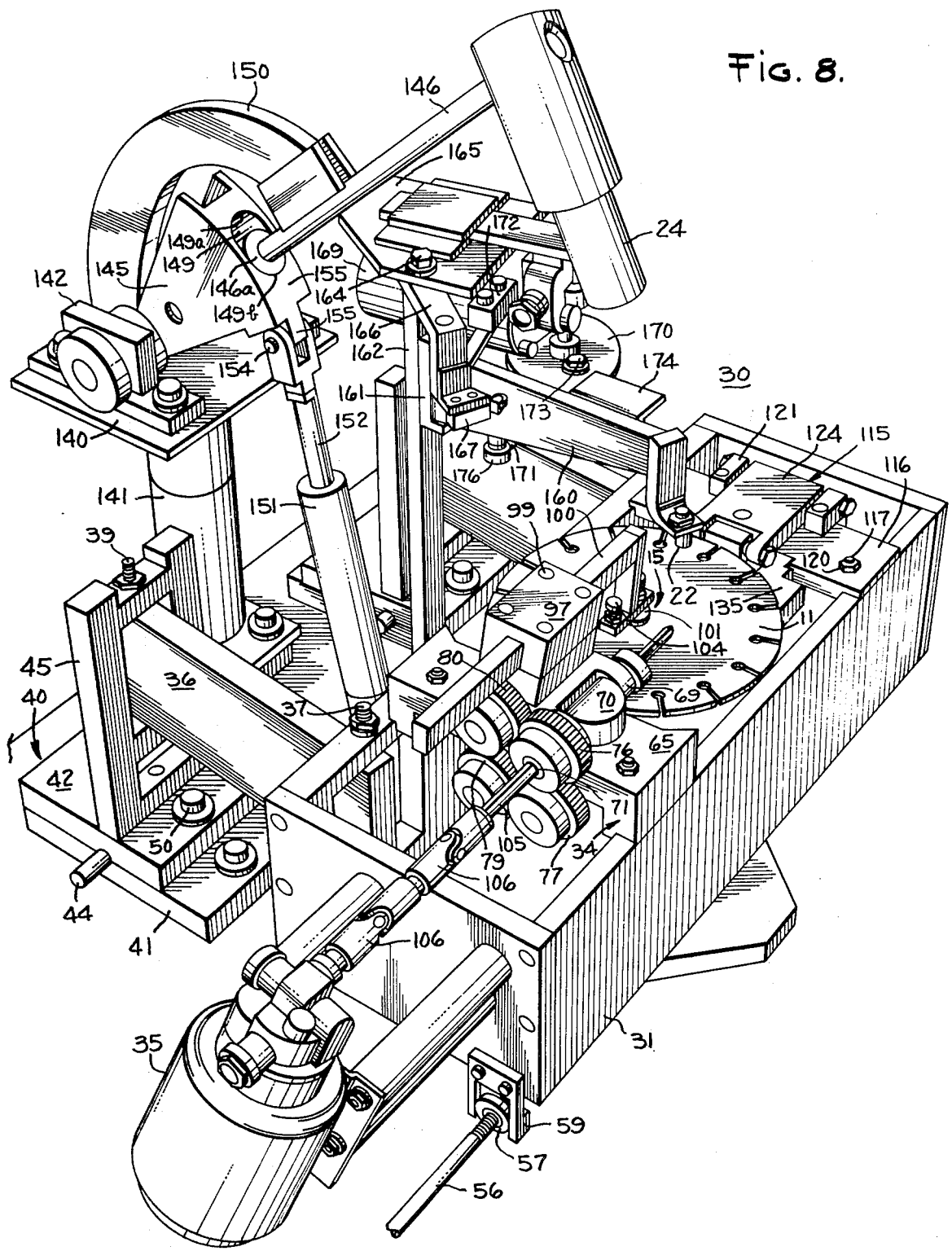
FIG. 8 is a view in perspective of a portion of a straightening and tensioning machine in accordance with this invention.

Referring now to the drawings, FIGS. 1–7 illustrate the principles upon which the improved method and machine for straightening and tensioning saws are based. A circular saw blade 11 may be held at one edge by a first supporting means 12 and by second supporting means 14 at an opposite edge. If a center-biasing means 15 is used to depress the central portion of the saw blade, it will be elastically bent about an axis parallel to a diameter so that its major surfaces lie in curved planes. This curvature is shown by the application of a straight edge 16 in FIG. 1. Note that in FIG. 1 the straight edge is supported at its end portions and that there is clearance under the central portion of the straight edge.

At right angles to a line connecting the first supporting means 12, center-biasing means 15, and second supporting means 14, no deflection would be evident in a properly tensioned saw blade, as is shown by a straight edge 17 in FIG. 2, which is in contact with the blade over the entire length of the straight edge.

By controlling the amount of relative vertical motion of the center-biasing means 15 and the supporting means 12 and 14, the displacement of the center of the saw blade 11 with respect to its outer edge can be precisely controlled. It should be noted however that, as will be discussed in greater detail subsequently, the exact curvature assumed by the saw blade 11 depends not only on the amount of displacement but upon other parameters of the saw, of particular significance being the distribution of tension within the saw.

During the manufacturing and heat treating steps to which a saw blade must be subjected, it is highly likely that an uneven distribution of residual tension stress will be produced and that certain areas, such as defects 19 and 20 illustrated in FIG. 3, will be produced wherein the tension is significantly greater or less than that in the surrounding areas of the saw blade. These defects may be of any shape or size and are not readily detectable in the saw. However, if the saw blade 11 is bowed in the manner shown in FIGS. 1 and 2, these defects become detectable. As shown diagrammatically in an exaggerated fashion in FIG. 4, when the saw blade 11 is deflected into a curved form, a tight surface area such as the defect 19 will tend to pull inwardly as a chord spanning a portion of the curvature because its tension is greater than that of the surrounding areas of the saw blade. Thus this portion will appear to be raised from the concave surface of the blade above its proper position, which is shown by a dashed line 19a in FIG. 4. A skilled craftsman can utilize a straight edge to detect this defect and map it on the surface of the saw so that he may subsequently cure the defect by hammering. It should be noted that a "loose" portion of the surface area, having less residual tension stress than the surrounding surface, would fall away from the natural curvature of the saw blade. However, such loose areas are relatively rare and tend to disappear as the relative tension of the rim of the saw is increased.

As was indicated in connection with FIGS. 1 and 2, the deflection of the center of the saw produced by the center-biasing means 15 with respect to the supporting means 12 and 14 can be precisely controlled. However, the precise curvature that the saw blade 11 will assume depends largely on the tension distribution in the saw. A dashed line 21 in FIG. 5 represents the curvature that would be assumed by a bowed saw having a desired tension distribution. The saw blade 11 illustrated in FIG. 5 does not, however, conform to the desired curvature 21; the central portion of the saw blade falls inside of this curve, while the rim of the saw blade extends outside. This represents a saw blade which is "loose on the outside", and may be corrected by hammering the inner portion of the blade to relieve tension in that area.

The saw blade 11 as illustrated in FIG. 6 also fails to conform to the desired curvature 21. Here, however, the inner portion of the saw remains outside the curve, while the rim falls inside. This is a configuration known as "loose in the center" and can be corrected by proper hammering near the rim of the saw.

These and other distortions and tensioning defects can be corrected by the use of a method and machine for tensioning and straightening saws in accordance with this invention. The theory of operation of this method and machine can be explained by reference to FIG. 7, which illustrates the circular saw blade 11 in the bowed configuration described in conjunction with FIGS. 1 and 2, held by supporting means 12 and 14 and dished by the center-biasing means 15. A sensor 22 is positioned at a predetermined distance over the saw blade 11. The sensor 22 may be of any type having sufficient sensitivity to detect the minute deviations in the distance to a small local area of the blade surface which are indicative of both surface distortions and tensioning defects. Either electrical, mechanical or pneumatic sensing may be utilized; in the preferred embodiment, the sensor 22 is a proximity detector of a type well-known in the art, capable of determining by electromagnetic induction whether a metallic object is at a preset distance from the sensor.

Bowing of the saw blade 11 into a predetermined curvature enables local defects as shown in FIGS. 3 and 4, and overall maldistribution of tension as shown in FIGS. 5 and 6, to be detected by the sensor 22. The sensor is maintained a predetermined distance from the saw, and its sensitivity is adjusted to detect any points on the surface of the saw that are closer to the sensor than would be found in a perfectly-tensioned and perfectly-straightened saw. The sensor and saw blade must then be moved relative to each other so that the sensor sweeps substantially the entire surface of the saw blade for such detection. It is sufficient to limit the detection to those points which protrude from the concave surface, and which represent either surface deformities or tight spots of excess tension. Loose spots of low tension are corrected by hammering the tight spots, since this redistributes the tension more uniformly.

The relative motion may be accomplished in many ways. The sensor may remain fixed while the saw blade is moved relative to the sensor, the sensor may be moved over the surface of the saw blade while the saw blade remains stationary, or a combination of motions of both the sensor 22 and the saw blade 11 may be used. In the preferred embodiment, the sensor traces a helical path in its examination of the surface of the saw blade. This form of path is particularly useful in view of the circular shape of the saw blade, as it provides the most efficient coverage of the surface of the saw with the simplest mechanical motions.

With the preferred manner of dishing the saw, it will be readily apparent that it would be complicated to have the sensor 22 move in a helical path over the surface of a stationary saw. The sensor 22 would have to be made to follow a complicated vertically reciprocating path as well as a helical horizontal path as it traveled around the surface of the blade. It should be noted, however, that were the saw blade 11 to be dished into the general form of a segment of an oblate spheroid, it might be a reasonable procedure to physically move the sensor in a helical path above the surface of a stationary saw.

The preferred method of examining the surface of the saw blade 11 is to rotate the blade about its center while maintaining the supporting means 12 and 14 in fixed positions, so that during each revolution each portion of the blade will be flexed successively into the configuration illustrated in FIG. 7, when in alignment with the supporting means 12 and 14 and the center-biasing means 15. If the blade is rotated while the blade and the sensor 22 are moved linearly with respect to each other so that the sensor effectively reciprocates or oscillates between the position of the second supporting means 14 and that of the center-biasing means 15, helical paths covering substantially the entire surface of the saw blade 11 will be traced by the sensor. This relative reciprocating action can be provided by physically moving either the sensor 22 or the saw blade 11.

An added requirement is that the distance from the sensor 22 to the warped plane of curvature of the surface of a properly-tensioned and straightened saw blade be kept constant, so that deviations from this plane due to tension and surface defects may be detected. Accordingly, the path of relative motion of the sensor 22 over the saw blade 11 must lie in a curved plane parallel to that of the ideal blade shown by the dashed line 21 of FIGS. 5 and 6, displaced, however, from the latter by the desired amount.

Preferably positioned in vertical alignment with the sensor 22 are a hammer 24 and an anvil 25. To maintain this alignment, the hammer and anvil must be moved with the sensor, in the case where the sensor 22 is physically moved with respect to the saw blade 11. The anvil 25 should not, however, be moved vertically; its upper surface 25a should be held in a predetermined vertical location, which will be further defined subsequently.

During the sensing of the saw blade 11 by the sensor 22, the relative helical motion of the sensor and blade continues without interruption, so long as the portions of the surface being sensed are not closer to the sensor 22 than the predetermined distance. However, whenever the sensor 22 detects a "high spot", i.e., a point on the blade closer to the sensor than the predetermined distance, relative motion of the sensor and saw blade stops. The sensor has now detected a point that must be hammered.

The high spot on the surface of the saw may represent a bend or kink, or a tight spot or surface discontinuity under excess tension, or the tighter portion of an improperly tensioned saw blade, such as the central portion shown in FIG. 5 or the outer portion shown in FIG. 6. Any of these effects can be corrected by hammering.

To accomplish the hammering, the saw blade 11 is lowered to the position shown as a dashed line in FIG. 7 at 11A. This may be accomplished by lowering the supporting means 12 and 14 to the positions shown as 12A and 14A, respectively. It should be noted, however, that since the release of the saw blade from its bowed form is done only to place the blade on the anvil 25, it is only necessary to lower the second supporting means 14. This action will place the portion of the saw blade to be hammered on the upper surface 25a of the anvil, which is maintained in a suitable position for that purpose.

Before the saw blade can be struck by the hammer 24, the sensor 22 must be removed from its sensing position. This can be done in substantially any direction and by any convenient means, so long as the sensor is outside the path of the hammer 24 when it is released. The hammer 24 is then released and falls, striking the saw blade sharply at the point where the high spot was detected. This point will be straightened if it is a physical bend in the saw, and will be loosened if it is a spot of excess tension.

The hammer 24 is then lifted from the saw blade 11. When the sensor 22 has been moved back to its operating position and the saw blade 11 again bowed by the supporting means and biasing means, sensing operation begins again. If the spot which has just been hammered still shows as a high spot, no relative motion of the sensor and blade will occur, and the hammering cycle will repeat itself until the spot conforms to the desired curvature. Once this has been accomplished, the relative sweeping motion of the sensor and saw blade resumes, being stopped again for the hammering of any further high spots that may be detected. After all discovered defects have been removed from one surface of the saw blade, it is turned over to treat the other surface. This treatment may be repeated as many times as desired, and with whatever sensitivity is deemed necessary, to accomplish the level of precision of tensioning and straightening needed for any particular saw blade.

The sensing and hammering operations preferably proceed from the outer edge of the saw blade toward the center. If a tight region or a bulge extends inwardly for some radial distance, hammering the outer portion tends to relieve the inner portion as well.

THE MACHINE - FIRST EMBODIMENT

Figure 9:
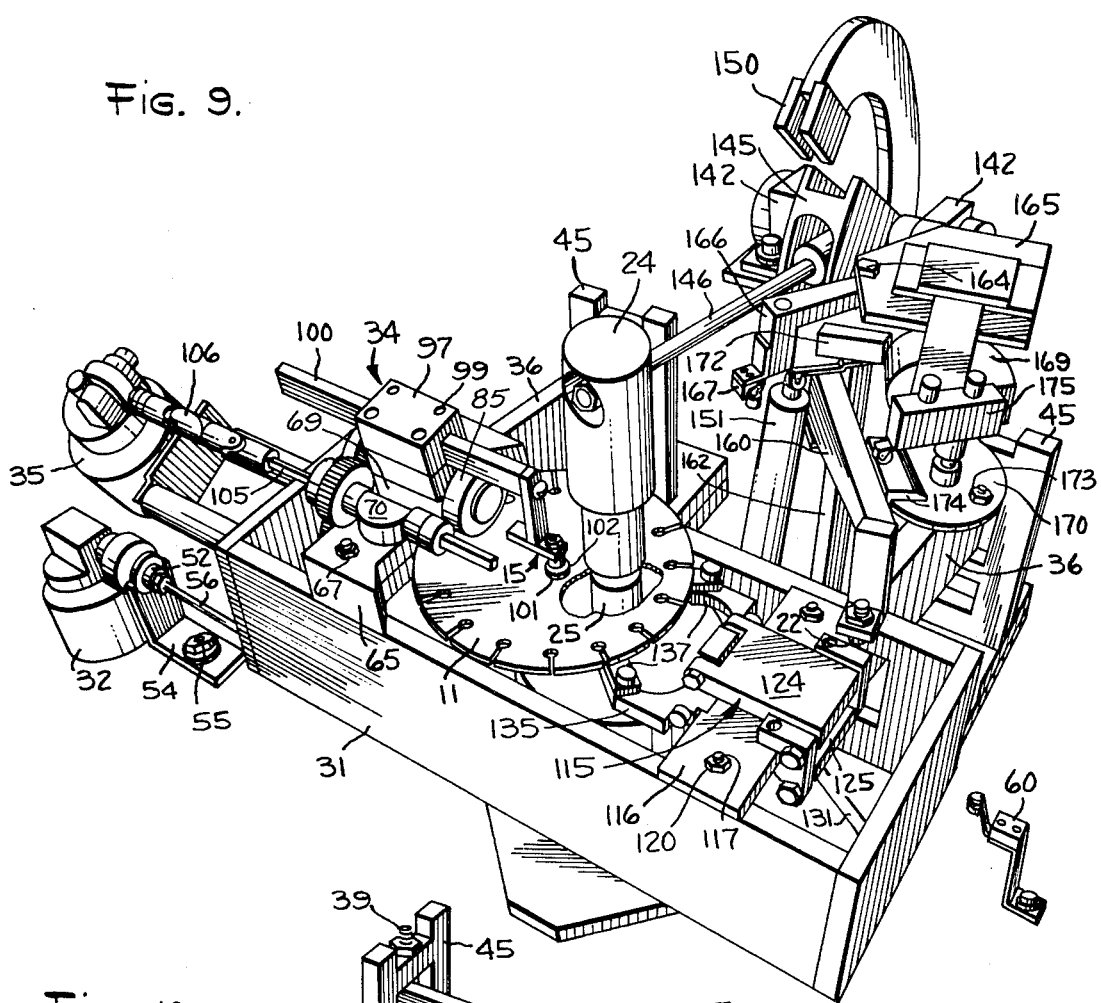
FIG. 9 is a view in perspective of the machine of FIG. 8, shown with a hammer striking a circular saw blade.

A preferred form of tensioning and straightening machine 30 in accordance with this invention is illustrated in FIGS. 8-17. In this embodiment, the hammer 24 and anvil 25 (see FIG. 9) remain fixed in position, as does the sensor 22 during sensing operations, while the circular saw blade 11 is moved with respect to these elements. To provide the relative movement required for sensing, the saw blade 11 is mounted on a carriage 31 which is driven in a reciprocating or oscillating motion by a motor 32 (FIG. 9). A saw blade drive assembly 34 is mounted on the carriage 31 and is driven by a motor 35 to provide circular motion for the saw blade 11.

Figure 10:
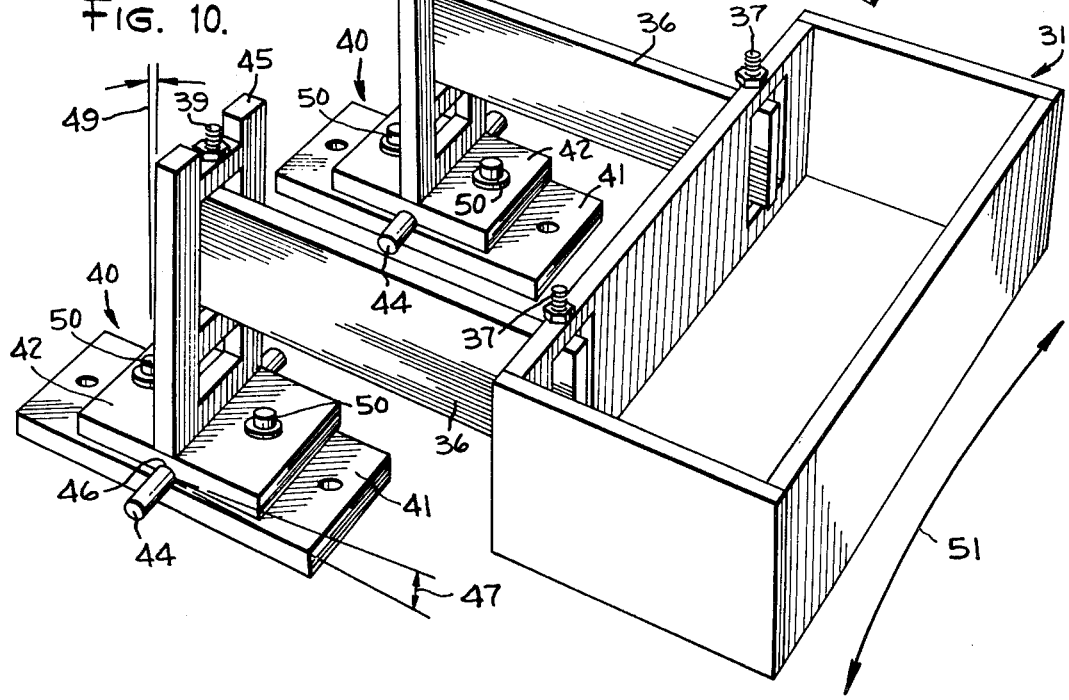
FIG. 10 is a view in perspective of a carriage of the machine of FIG. 8.

The carriage 31, as is best shown in FIG. 10, is preferably constructed of metal and may be of any convenient shape and size adequate for mounting the necessary components for stressing and rotating the saw blade. The carriage 31 is connected to a pair of parallel carriage arms 36 by a pair of hinge bolts 37. The carriage arms 36 are connected at their other ends by an additional pair of hinge bolts 39 to a pair of substantially identical carriage mount assemblies 40. To provide free lateral reciprocating motion of the carriage 31 with respect to the carriage mount assemblies 40, care should be taken to see that the hinge bolts 37 and 39 are all parallel to each other.

Each carriage mount assembly 40 preferably comprises a lower mounting plate 41, an upper mounting plate 42, a pivot rod 44 and a mounting frame 45. The mounting frame 45 is attached to the carriage arm 36 by the hinge bolt 39 and is secured to the upper mounting plate 42 in a manner to prevent any relative motion between the mounting frame 45 and upper mounting plate 42. The lower mounting plate 41 may be bolted or otherwise attached to any suitable base. In the preferred embodiment, corresponding grooves 46 are provided in an upper surface of the lower mounting plate and a lower surface of the upper mounting plate to accommodate the pivot rod 44. The combined depths of the grooves should be, however, less than the diameter of the pivot rod 44 so that, absent other securement, the upper mounting plate would rock back and forth on the lower mounting plate with the pivot rod 44 being the pivot.

This construction permits the upper mounting plate 42 to move through an angle, shown as 47, with respect to the lower mounting plate. Because the mounting frame 45 is integrally secured to the upper mounting plate 42, it, in turn, can move through an equivalent angle shown as 49. By this arrangement, the mounting frame can be placed at any desired inclination with respect to the vertical, within the range of the angle 49, for reasons which will be subsequently explained. With the mounting frame in the desired position, a pair of bolts 50, positioned at opposite sides of the pivot rod 44, are tightened through openings in the upper mounting plate 42 into threaded openings in the lower mounting plate 41, thus pulling against each other to fix the position of the upper mounting plate 42 and, accordingly, the mounting frame 45.

To maintain the desired parallel alignment of the hinge bolts 37 and 39, each of the mounting frames 45 must be positioned at the same angle with respect to the vertical. It should be readily apparent from an examination of FIG. 10 that the carriage 31, swinging on the carriage arms 36, will sweep a generally circular path with respect to the mounting frames 45. If the carriage mount assemblies 40 are adjusted so that the mounting frames 45 and thus the hinge bolts 37 and 39 are exactly vertical, the entire circular motion of the carriage 31 will be in a horizontal plane having no vertical displacement, as it moves from one end of its sweep to the other. If the mounting frames 45 are shifted through an angle from the vertical in the manner previously described so that the hinge bolts 37 and 39 are also shifted from the vertical, the carriage will maintain the same circular motion with respect to the mounting frames 45. However, the circle through which the carriage moves will no longer be in a horizontal plane. There will be a definite and controllable vertical displacement, generally tracing a portion of an ellipse when projected on the horizontal plane. If the frames 45 are tipped backwardly in a counterclockwise direction as shown in FIG. 10, the low points of carriage movement are reached when the arms 36 are swung to their extreme positions, and the carriage attains its highest point when the arms are midway between their extremes as shown. The carriage sweeps an oscillatory path as suggested by the arrow 51. The bowed bow blade is lower in the center than at the edges, as shown in FIG. 7. By properly adjusting the angle at which the frames 45 are inclined to the vertical, the carriage 31 can be made to follow a path which is an inverted image of the curvature of the bowed saw blade. With a properly tensioned saw blade having no substantial surface defects, the swinging motion of the carriage and a blade mounted thereon cancels out the curvature of the blade and maintains a constant distance between the stationary sensor and the surface of the moving blade. The sensor thereby responds only to defects in the blade, and is unaffected by the curvature caused by intentional bending.

The carriage motor 32 which provides the reciprocating motion of the carriage 31 is mounted on a gimbal 52 pivoted in a mounting bracket 54, which is independently attached to the base by a bolt 55 or other fastener. A carriage drive shaft 56 is threaded into a gimbal nut 57 (FIG. 8), which is pivoted in a mounting bracket 59 on the carriage 31. The extent of the sweep of the carriage 31 in either direction is controlled by a limit switch 60 (FIG. 9) and a limit switch 61 (FIG. 11), which are independently mounted on the base and positioned to be operated by the approach of opposite ends of the carriage 31. The mode of operation of the limit switches 60 and 61 will be described in detail in the discussion of FIG. 17. When the carriage 31 interacts with either limit switch 60 and 61, the carriage motor 32 is reversed, causing a change in the direction of rotation of the carriage drive shaft 56. Because this drive shaft is threaded through the gimbal 57 on the carriage 31, this change in its rotation causes a reversal in the direction of motion of the carriage 31. In this manner an oscillating motion of the carriage 31 is provided, the gimbals 52 and 57 preventing jamming or misalignment of the carriage drive shaft 56 which might otherwise be produced by the arcuate motion of the carriage.

Figure 12:
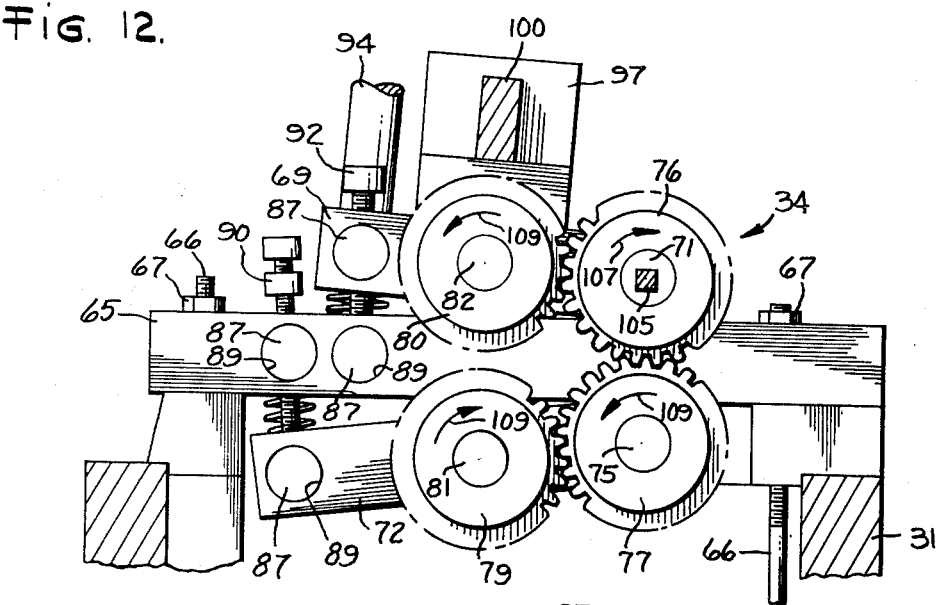
FIG. 12 is a fragmentary view in left side elevation of a saw blade drive means of the machine of FIG. 8.
Figure 13:
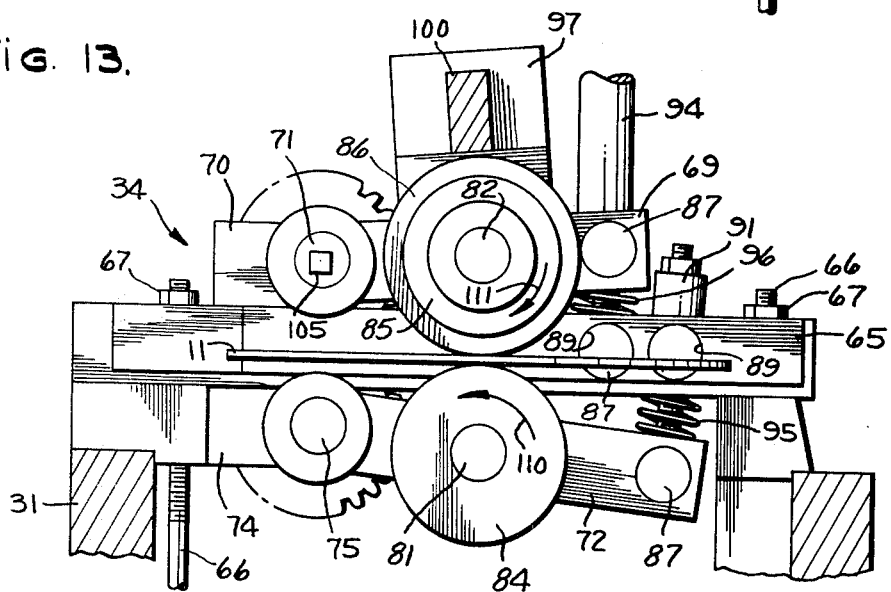
FIG. 13 is a fragmentary view in right side elevation of the saw blade drive means of FIG. 12.

The saw blade drive assembly 34 is best illustrated in FIGS. 12 and 13 and has a base 65 which is machined to rest on opposite parallel sides of the carriage 31. The base may accordingly be positioned in any desired location on the carriage 31 to accommodate saws of various diameters, in a manner to be later described herein. The base 65 is clamped in position on the carriage 31 by placing a clamping bar (not shown) beneath the carriage and fitting a pair of elongated clamping bolts 66 through aligned openings in the clamping bar and base. By tightening a pair of nuts 67, the base 65 and clamping bar are pulled toward each other, locking the saw blade drive assembly 34 in position on the carriage 31 in a well-known manner.

An upper drive arm 69 has a pair of ears 69a (see FIG. 11) at one end and is secured to an upper attachment lug 70 by a shaft 71 passed through corresponding openings in the ears 69a and the upper attachment lug. This means of attachment permits pivotal motion between the upper drive arm 69 and the base 65. A lower drive arm 72 shown in FIGS. 12 and 13 is similarly constructed and is attached to a lower attachment lug 74 on the base 65 by a shaft 75 to permit pivot motion between the lower drive arm and the base.

Mounted on the shaft 71 on one side of the saw blade drive assembly 34, as shown in FIG. 12, is a drive gear 76. Driven gears 77, 79 and 80 are mounted, respectively, on the shaft 75 and shafts 81 and 82.

On the side of the saw blade drive assembly 34 opposite the gears 76-80 (see FIG. 13) are a lower drive wheel 84 and an upper drive wheel 85 which are mounted, respectively, on the shaft 81 and the shaft 82 and are positioned to engage the rim of the circular saw blade 11 therebetween to produce rotation of the blade. The lower drive wheel 84 is preferably a solid metallic part while the upper drive wheel 85 preferably has an outer rim 86 of rubber or other suitable cushioning material.

Both the upper drive arm 69 and lower drive arm 72 must be accurately fixed in position to firmly engage the saw blade 11 between the drive wheels 84 and 85, and to locate the blade precisely. To this end, adjustable attachment means are used to position and hold the drive arms 69 and 72 in place. These are preferably attached to cylindrical rods 87 which are rotatably received in holes 89 in the arms and the base 65. By securing the attachment means to these rods, proper alignment of threaded openings with threaded members can be maintained regardless of the relative angles the drive arms 69 and 72 make with the base 65.

A spacer bolt 90 (FIG. 12) is threaded through a pin 87 in the base 65 and abuts the lower drive arm 72 to adjustably define the upper limit of travel of this arm. A draw bolt 91 (FIG. 13) passes freely through an unthreaded opening in the base 65 and is threaded into a pin 87 in the lower drive arm 72. Upon being tightened, the bolt 91 draws the lower drive arm firmly against the spacer bolt 90, fixing the arm in adjusted position.

The lower limit of travel of the upper drive arm 69 is adjustably fixed by a spacer bolt 92 (FIG. 12), which is threaded through a pin 87 in this arm and abuts the base 65. A nut 94 is threaded on a stud 93 which passes freely through the arm 69 and is fixed in a pin 87 in the base 65. Tightening the nut 94 draws the upper drive arm 69 against the spacer bolt 92. If desired, compression springs 95 and 96 may be placed around the draw bolt 91 and the stud 93, respectively, to spread the drive arms from the base when the draw bolt 91 and the nut 94 are loosened. It should be noted that it may be convenient to replace the nut 94 and stud 93 with a more rapid clamping device, such as an air-operated actuator, to provide for more rapid attachment and release of circular saw blades 11 in the drive assembly 34.

Figure 11:
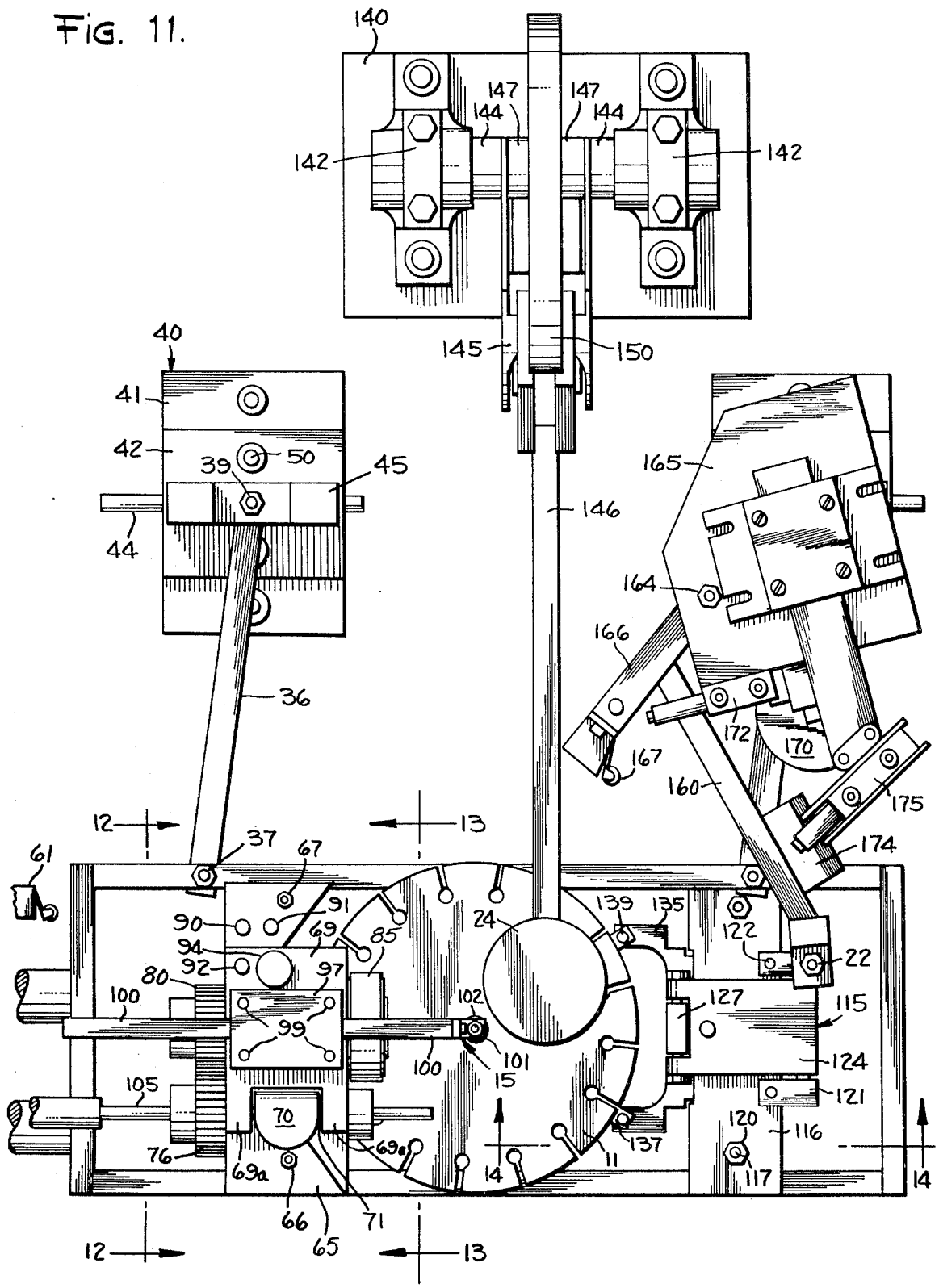
FIG. 11 is a top plan view of the machine of FIG. 8.

A metal block 97 is secured to the upper drive arm 69 by a plurality of threaded fasteners 99 (see FIG. 11) to hold an elongated positioning bar 100 of the center biasing means 15 in place. The center biasing means 15 is best illustrated in FIGS. 9 and 11, and has a center stud 101 which is attached at one end of the positioning bar 100 and is of an appropriate size to fit into a center hole of the circular saw blade 11. A peripheral lip 102 may be provided on the center stud 101 to perform the center biasing function previously described with reference to FIG. 7. However, with some saws it may be desirable to utilize the center stud 101 solely for fixing the position of the center of the saw blade 11, and to utilize a separate biasing means such as the screw 104 illustrated in FIG. 8 to perform the bowing function. Such separate biasing means might be useful with saws having diamond or other shape knockouts at the center, such saws being familiar to those skilled in the art. As the center biasing means 15 is affixed to the upper drive arm 69, the nut 94 controls not only the clamping of the saw blade between the drive wheels 84 and 85, but also the positioning and center biasing of the saw blade 11 by the center biasing means.

Operating power for the drive wheels 84 and 85 is conveyed by a drive shaft 105 (see FIG. 8, 9 and 12) which is keyed into the shaft 71 of the drive gear 76. The drive shaft 105 may be connected through a pair of universal joints 106 to prevent alignment problems with respect to the saw blade drive motor 35. The motor 35 may be secured to the carriage 31 as shown in FIG. 8, or may alternatively be mounted directly on the saw blade drive assembly 34.

Because the center biasing means 15 fixes the position of the center of the saw blade, the saw blade 11 may be rotated in the desired manner by moving the rim in either direction between the drive wheels 84 and 85. The adjustability provided for the upper drive arm 69 and the lower drive arm 72 by the spacer bolts 90 and 92, the draw bolt 91, and the nut 94 permits proper alignment of the drive wheels 84 and 85 with the surfaces of the saw blade. To prevent any distortion of the saw blade as it is being rotated, it is desirable that the centers of the drive wheels be vertically aligned with each other. If the centers are not in vertical alignment, the rim of the saw blade might be twisted, causing errors in the hammering operation. After the desired position for the lower drive arm 72 has been determined, it is preferably tightened and kept in place; when saw blades of different thicknesses are to be hammered, the upper drive arm 69 is loosened, adjusted to the proper height, and re-tightened.

After tightening the nut 94 with a saw blade 11 in place as shown in FIG. 13, the drive motor 35 is actuated to rotate the saw blade about the center stud 101 of the center biasing means 15. Motion is translated from the motor 35 to the saw blade 11 by the drive shaft 105, which turns the drive gear 76 in a direction shown, for example, by an arrow 107 in FIG. 12. The drive gear 76 causes the driven gears 77, 79 and 80 to rotate in directions shown by arrows 109. Motion of the driven gear 79 is passed by the shaft 81 to the lower drive wheel 84, which rotates in a direction shown by an arrow 110 in FIG. 13. Motion of the driven gear 80 is translated through the shaft 82 to the upper drive wheel 85, which rotates in a direction shown by an arrow 111 in FIG. 13. The drive wheels 84 and 85 rotate in opposite angular directions so that adjacent portions of the drive wheels more in the same linear direction, rotating the saw blade 11 in the desired manner.

It should be noted that the lower drive wheel 84 performs the function described for the first support means 12 of FIG. 1, in addition to aiding in the rotation of the saw blade 11. The function of the second supporting means 14 is performed by a saw blade lift assembly 115 best illustrated in FIGS. 14-16.

The saw blade lift assembly 115 has a base 116 which is preferably mounted on the carriage 31 in a manner substantially identical to the mounting of the base 65 of the saw blade drive assembly 34. The base 116 is placed on the carriage 31 in the manner illustrated in FIG. 8 and clamping bolts 117 are passed through openings in a clamping bar (not shown) beneath the carriage 31 and through openings 119 (FIG. 16) in the base 116. Nuts 120 (FIGS. 8 and 9) tighten the base 116 against the clamping bar to hold the saw blade lift assembly 115 firmly in position.

One or more substantially vertical mounting beams 121 are securely attached to the base 116 by threaded fasteners 122 passed through a mounting ear 121a on each beam 121. An upper cross beam 124 and a lower cross beam 125 are pivotally mounted by connectors 126 to the mounting beam 121. A vertical operating beam 127 is pivotally attached by connectors 129 to the upper cross beam 124 and lower cross beam 125.

Attached to the base 116 is a pair of air cylinder mounting legs 130 to which an air cylinder 131 is pivotally attached by a connector 132. An operating rod 134 of the air cylinder 131 is pivotally attached to the lower cross beam 125.

The mounting beam 121, upper cross beam 124, lower cross beam 125 and operating beam 127 form a pivotally-connected parallelogram linkage, so that when compressed air is supplied to the air cylinder 131 to force the operating rod 134 upwardly, the beams 124, 125 and 127 pivot upwardly with respect to the mounting beam 121 attached to the base 116. The beam 127 remains in its vertical orientation and undergoes very little horizontal displacement through the short arc of its travel.

Attached to the operating beam 127 is a bifurcated lift member 135. A pair of lift screws 136 may be mounted directly in the lift member 135 or, as shown, in a pair of extension legs 137 attached to the lift member by fasteners 139.

The use of extension legs 137 to hold the lift screws 136 affords great versatility to the saw blade lift assembly 115. As was explained with respect to FIGS. 1 and 2, the saw blade lift assembly 115, acting in conjunction with the center stud 101 of the center biasing means 15 and of the lower drive wheel 84 of the saw blade drive assembly 34, provides the desired bowed curvature to permit sensing of the saw blade 11. As will be explained further, the saw blade is sensed over a portion of its surface extending substantially from the center stud 101 to the saw blade lift assembly 115, so that the relative elevations and positions of the lift screws 136 are very important to proper tensioning and straightening.

One advantage ensues simply from the use of two lift screws. This permits the sensor 22 to examine points located between the lift screws rather than over them, so that it is highly unlikely that a defect riding over one lift screw will produce errors in the readings of the sensor, although such a problem could easily occur if a single lift screw were utilized. For example, if a ridge or bump protruding from the upper surface of the saw blade were to pass over a single lift screw positioned directly beneath the sensor, the correspondingly-concave lower surface of the sawblade resting on the lift screw would permit the upper surface, although deformed, to remain at the proper distance from the sensor. By the use of two separated lift screws 136, the lower surface is supported at points removed from the sensed region, so that when a defect passes under the sensor it will be correctly detected.

The use of extension legs 137 also permits the lift screws 136 to be positioned either close together or far apart, as may be required to best accommodate a wide variety of saw diameters. This gives the tensioning and straightening machine 30 greater versatility.

The relative heights of the lift screws 136 can be adjusted to permit fine adjustment of the curvature of the saw blade 11, thereby adding to the ability of the machine to accurately match the curvature of a properly straightened and tensioned saw to the reversed image of the sweep of the carriage.

Figure 14:
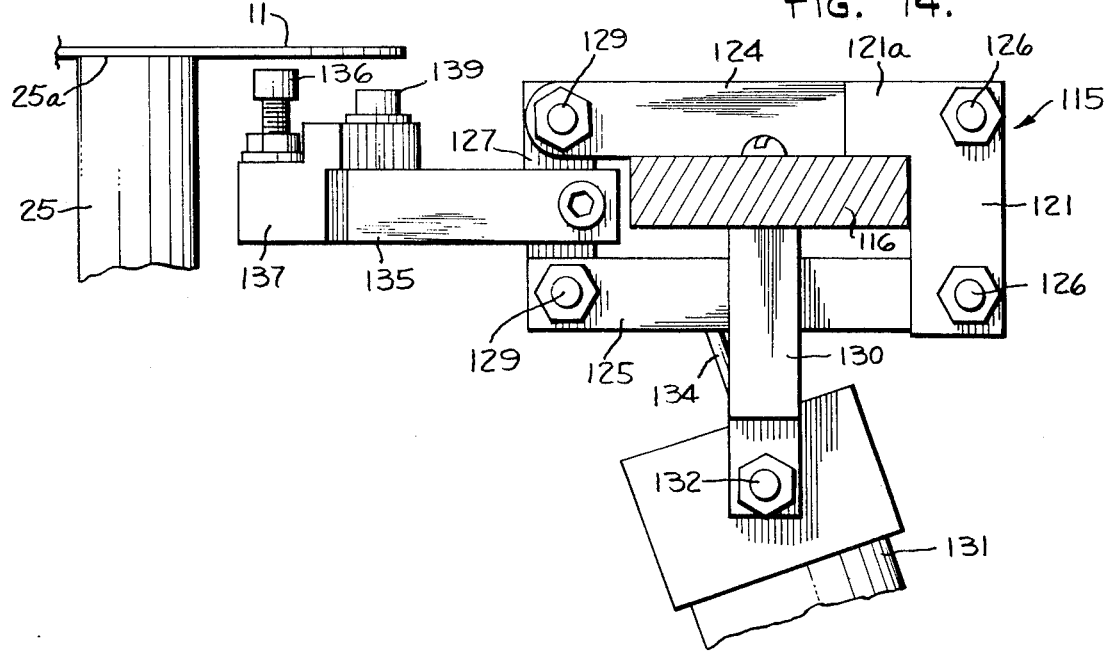
FIG. 14 is a fragmentary side view, partially in section, of a saw blade-deflecting means of the straightening and tensioning machine of FIG. 8, with the saw blade lowered onto an anvil.

When a saw blade 11 is placed on the carriage 31, the saw blade lift assembly 115 is positioned as shown in FIG. 14, with the lift screws 136 lowered beneath the level of the upper surface 25a of the anvil 25. In this position, the saw blade 11 is undistorted, and rests firmly and squarely on the anvil 25. When it is desired to sense the saw blade 11, the air cylinder 131 is activated so that the operating rod 134 pushes upwardly and the lift screws 136 lift the edge of the saw blade 11 from the anvil 25. The blade, being held by the center stud 101 and the wheel 84, is bent by the lift screws into a predetermined bowed curvature. When a defect is found on the surface of the saw blade 11 so that hammering is required, the air pressure is released from the air cylinder 131 so that the saw blade lift assembly 115 returns to the position shown in FIG. 14 and the saw blade 11 is released to drop onto the anvil 25.

The hammer 24 and its associated operating hardware are best illustrated in FIGS. 8, 9 and 11. A mounting plate 140 is rigidly affixed to a supporting pillar 141, which is in turn firmly mounted independently of the carriage 31. A pair of bearings 142 are attached to the mounting plate 140 and pivotally hold a pivot arm 144 of a striker block 145 therein. The hammer 24 is mounted on a shaft 146. The shaft 146 is attached to a pivot arm 147 (FIG. 11) which is journaled in bearings (not shown) within the pivot arm 144 of the striker block 145. By this construction, the hammer 24 is enabled to pivot independently of the striker block 145 while moving arcuately about the same axis.

An elastomeric bushing 146a is mounted on the shaft 146 and positioned in an opening 149 in the striker block 145. The opening 149 is somewhat angularly elongated, and has an upper surface 149a and a lower surface 149b having contours substantially matching those of the bushing 146a. The bushing 146a provides cushioning during impact of the striker block 145 against the shaft 146, but is sufficiently firm to avoid materially lessening the impact of the hammer 24 against the saw blade 11. A magnet 150 is attached to the mounting plate 140 for normally holding the shaft 146 of the hammer 24 in its fully raised position as shown in FIG. 8.

An air cylinder 151 is independently attached to the base of the machine, and has an operating rod 152 which is connected by a suitable pin 154 or other pivotal attachment means to an ear 155 on the striker block 145. The air cylinder 151 is preferably of the double-acting type, having air hoses connecting either side of an internal operating piston to a suitable valve (not shown) of a type which is operable to drive the operating rod 152 selectively in an upward and downward direction. Such an arrangement is well known to those skilled in the art, and will not be described further.

While the sensor 22 is scanning the saw blade 11, the hammer 24 is held in the raised position shown in FIG. 8 by two independent means. The magnet 150 holds the shaft 146 with sufficient force to prevent the hammer 24 from falling. Additionally, the air cylinder 151 maintains the operating rod 152 in its uppermost position so that the shaft 146 is supported by the lower surface 149b of the opening 149 in the striker block 145. When a defect in the blade has been sensed, the sensor 22 is removed from its position above the saw blade 11 and the saw blade is lowered onto the anvil. Then a valve is actuated which causes the air cylinder 151 to pull down sharply on the operating rod 152, accelerating the striker block 145 downwardly. However, it should be noted that the hammer 24 remains in place, supported by the magnet 150, until the striker block 145 has moved a sufficient distance so that the upper surface 149a of the opening 149 strikes the bushing 146a on the shaft 146. When this occurs, the hammer 24 is snapped downwardly, firmly striking the saw blade 11 as it reaches the lowered position illustrated in FIG. 9.

After the hammer 24 has struck the saw blade, the control valve is actuated to cause the air cylinder 151 to force the operating rod 152 upwardly, raising the striker block 145. The lower surface 149b of the opening 149 pushes upwardly on the bushing 146a so that the hammer 24 is raised back into the position shown in FIG. 8. Upward motion of the striker block 145 is stopped when the shaft 146 comes into contact with the magnet 150.

The sensor 22 and means for mounting it and controlling its operation are best illustrated in FIGS. 8, 9, and 11. The sensor is mounted on a sensor arm 160, which is pivotally supported on a hinge bracket 161 (FIG. 8) attached to an independent supporting pillar 162, for arcuate movement in a generally horizontal plane. Attached to the top of the pillar 162 by a bolt 164 are a sensor drive motor mounting plate 165 and a sensor drive switch mounting arm 166. A sensor drive switch 167 is attached to the mounting arm 166.

A sensor drive motor 169 is attached beneath the mounting plate 165. A crank 170, which may be in the form of a disk (as shown) or a rod, is drivingly connected with the sensor drive motor 169 to convert its rotary output into reciprocating motion in a well-known manner. A sensor drive rod 171 (FIG. 8) is pivotally connected at 173 and 176 with the crank 170 and the sensor arm 160, respectively, so that the reciprocating motion produced by the crank 170 is imparted to the arm 160 and sensor 22.

When the sensor 22 reaches its operating position over the saw blade 11, as shown in FIG. 8, the sensor arm 160 abuts the sensor drive switch 167 which, as will be hereinafter described, stops the annular motion of the sensor arm toward the center of the saw blade. Accordingly, it can be seen that the location of the sensor drive switch 167 determines the operating position of the sensor 22.

When the sensor 22 detects a defect which must be hammered, the sensor drive motor 169 is actuated to turn the crank 170 in an angular direction which causes the sensor drive rod 171 to retract the sensor arm 160 and sensor away from their operating positions over the saw blade. An air switch 172 is mounted to be actuated by motion of the sensor arm 160 shortly after it begins its retracting movement away from the saw blade 11. The air switch 172 is connected through suitable hoses and valves (not shown) to the air cylinder 131 of the saw blade lift assembly 115 in such fashion that the retraction of the sensor arm 160 releases pressure from the air cylinder, so that the saw blade lift assembly 115 lowers the saw blade onto the anvil 255 and into the undeflected position illustrated in FIG. 14.

As the sensor arm 160 reaches the outward limit of its travel as shown in FIG. 9, a camming plate 174 attached to the arm actuates an air switch 175, which is connected by suitable hoses and valves (not shown) to the air cylinder 151 that operates the hammer 24. Actuation of the air switch 175 causes the hammer 24 to strike the saw blade 11 in the manner previously descibed. It should be noted that the hammer thus cannot be caused to strike the saw blade until the arm 160 and sensor 22 have been completely removed from its path.

Upon reaching the end of the retracting motion, the direction of travel of the sensor arm 160 is reversed by continued rotation of the crank 170, withdrawing the camming plate 174 from the air switch 175. This actuates the air cylinder 151 to raise the hammer back to the position shown in FIG. 8, where it is supported both by the pressurization of the air cylinder 151 and the attraction of the magnet 150.

Figure 15:
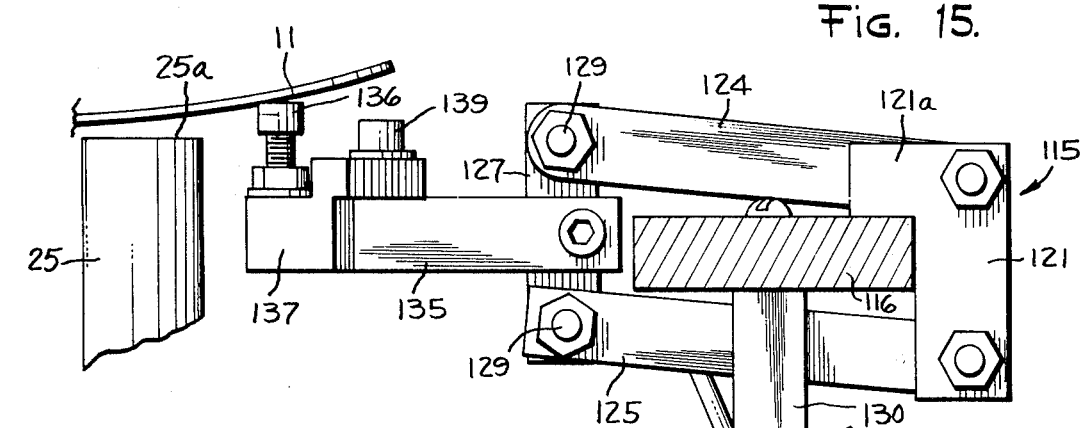
FIG. 15 is a fragmentary side view, partially in section, of the saw blade-deflecting means of FIG. 14, showing the saw blade held in a deflected configuration.

The continuation of the motion of the sensor arm 160 toward the center of the raw blade 11 causes the arm to engage the air switch 172, pressurizing the air cylinder 131 to lift the saw blade 11 into a bowed configuration raised from the anvil 25, as shown in FIG. 15. It is desirable that the saw blade be deflected into this configuration prior to the sensor 22 reaching its operating position, so that vibrations which may be produced in the saw blade when it is lifted can damp out naturally before the sensing operation beings. Owing to the high sensitivity of the sensor 22, a vibration in the saw blade might otherwise be detected as a defect and inadvertently hammered.

Continuing motion of the sensor arm 160 brings the sensor 22 to its operating position over the saw blade. At this point, the sensor arm 160 engages the switch 167, deenergizing the sensor drive motor 169 to stop the motion of the sensor. The sensing operation, which will later be described, then begins.

THE CONTROL CIRCUIT

Figure 17:
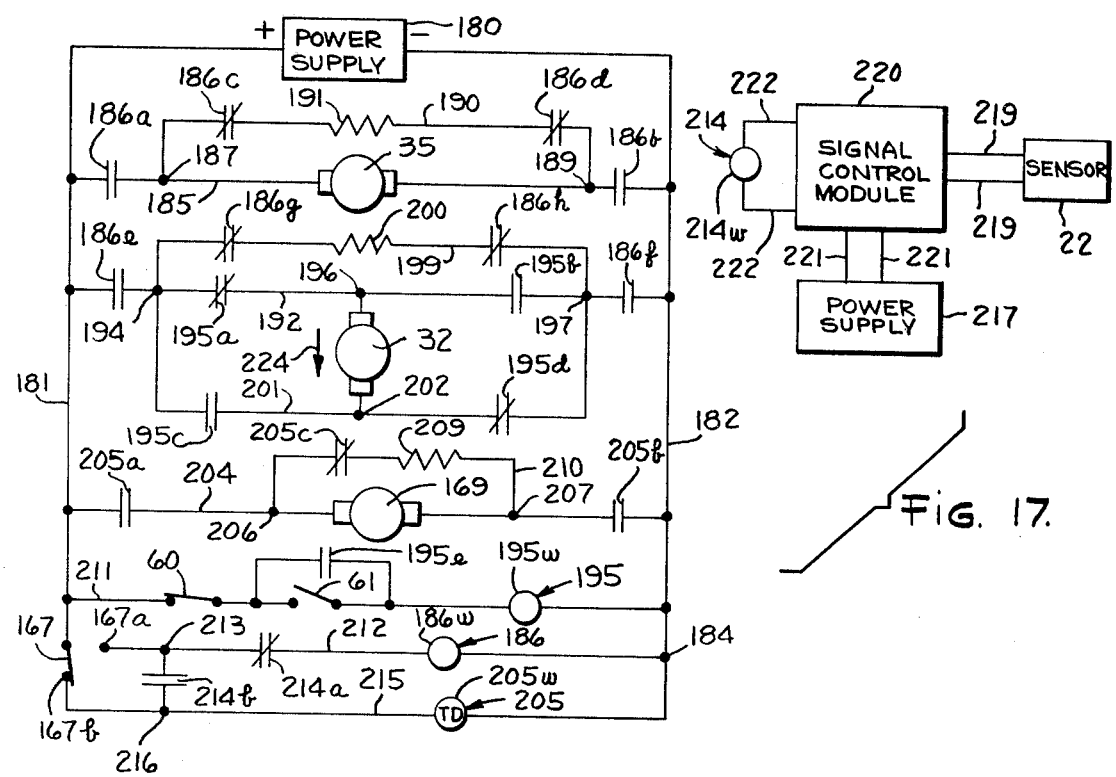
FIG. 17 is a schematic diagram illustrating electrical circuitry for the machine of FIG. 8.

The electrical circuitry for controlling the operation of the tensioning and straightening machine is illustrated in FIG. 17. A direct current power supply 180 provides operating power for the motors and relays. It should be noted, however, that other embodiments may utilize alternating current for powering relays or motors. A conductor 181 connects one terminal of the power supply 180 to the sensor drive switch 167. A conductor 182 connects the other terminal of the power supply 180 to a junction 184.

A conductor 185 is connected from the conductor 181 through a normally open contact 186a of a relay 186, a junction 187, the armature of the saw blade drive motor 35, a junction 189, an a normally open contact 186b of the realy 186, to the conductor 182. Each of the motors is preferably shunt wound and has a separately excited field. A conductor 190 serially connects a normally closed contact 186c of the relay 186, a resistor 191 and a normally closed contact 186d of the relay 186 between a junction 187 and a junction 189 with a conductor 185.

A conductor 192 is connected from the conductor 181 through a normally open contact 186e of the relay 186, a junction 194, a normally closed contact 195a of a relay 195, a junction 196, a normally open contact 195b of the relay 195, a junction 197, and a normally open contact 186f of the relay 186, to the conductor 182. Serially connected between the junction 194 and the junction 197 by a conductor 199 are a normally closed contact 186g of the relay 186, a resistor 200, and a normally closed contact 186h of the relay 186. Serially connected between the junctions 194 and 197 by a conductor 201 are a normally open contact 195c of the relay 195, a junction 202, and a normally closed contact 195d of the relay 195. The armature of the carriage motor 32 is connected between the junction 196 and the junction 202.

A conductor 204 is connected between the conductors 181 and 182 and serially connects a normally open contact 205a of a time delay relay 205, a junction 106, the armature of the sensor drive motor 169, a junction 207 and a normally open contact 205b of the time delay relay 205. A normally closed contact 205c of the time delay relay 205 and a resistor 209 are serially connected by a conductor 210 between the junctions 206 and 207.

A conductor 211 serially connects the normally closed limit switch 60, the normally open limit switch 61, and the winding 195w of the relay 195, between the conductors 181 and 182. A normally open contact 195e of the relay 195 is connected across the limit switch 61.

The sensor drive switch 167 is a single-pole double-throw switch having terminals 167a and 167b. The terminal 167a is connected by a conductor 212 through a junction 213, a normally closed contact 214a of a sensor relay 214, and a winding 186w of the relay 186, to the junction 184. A conductor 215 connects the terminal 167b of the sensor drive switch through a junction 216 and a winding 205w of the time delay relay 205 to the junction 184. A normally open contact 214b of the sensor relay 214 is connected between the junction 213 and the junction 216.

The sensor 22 is independently controlled and is powered by a low voltage power supply 217. The sensor is connected by conductors 219 to a signal control module 220, which is connected by conductors 221 to the power supply 217 and by conductors 222 to a winding 214w of the sensor relay 214. The signal control module 220 controls energization of the sensor 22 from the power supply 217, while the output of the sensor controls energization of the winding 214w of the sensor relay 214 by the signal control module.

Operation of the circuitry of FIG. 17 will now be described. The power supplies 180 and 217 are turned on, energizing the circuits. If the sensor 22 and its arm 160 are in the operating position illustrated in FIG. 8, and the sensor is over a portion of a saw blade whose surface coincides with the predetermined desired curvature, the sensor 22 will produce no output, and the winding 214w of the sensor relay 214 will not be energized.

The determination of which of the motors 32, 35 and 169 are energized ultimately depends on whether the winding 186w of the relay 186 or the winding 205w of the time delay relay 205 is energized. It can be seen that this is determined by the condition of the sensor drive switch 167. With the sensor arm 160 in the operating position shown in FIG. 8, the sensor drive switch 167 is biased by the arm so that contact is made with the terminal 167a. Thus, the relay 186 is energized by a circuit from the power supply 180 through the conductor 181, the sensor drive switch 167, the closed sensor relay contact 214a, the conductor 212, the winding 186w, and the conductor 182. defect When the winding 186w is energized, normally open contacts 186a, b, e and f are closed and normally closed contacts 186c, d, g and h are opened. This completes a circuit energizing both the carriage motor 32 and the saw blade drive motor 35. Resistors 191 and 200 are disconnected from across the motors 35 and 32, respectively. The sensor drive motor 169 is not energized because the contacts 205a and 205b remain open. Thus, when the sensor arm is in the operating position shown in FIG. 8 and no defect has been detected by the sensor 22, the saw blade drive motor 35 operates to rotate the saw on the carriage, and the carriage motor 32 operates in one direction of rotation to sweep the carriage, and thus the saw blade 11, past the sensor 22. The sensor drive motor 169 does not operate, so the sensor arm 160 and the sensor 22 remain fixed in the operating position.

As has previously been described, the direction of motion of the reciprocating carriage 31 is controlled by the direction of rotation of the carriage drive shaft 56 and the carriage motor 32. The relay 195 functions as a reversing switch for controlling the direction of armature rotation of the carriage motor 32. Operation of the reversing relay 195 is controlled by the limit switches 60 and 61.

During an initial phase of operation, the winding 186w of the relay 186 is energized to operate the motors 32 and 35, but the winding 195w of the reversing relay 195 is not energized, being open circuited by the normally open contact 195e and the normally open limit switch 61. Accordingly, the contacts 195a and 195d are closed, the contacts 195b and 195c are open, and current flows from the power supply 180 through the conductor 181, the conductor 192, the contact 186e, the contact 195a, the carriage motor 32, the conductor 201, the contact 195d, the contact 186f, and the conductor 182 back to the power supply. It can be seen that current flow through the carriage motor 32 is in the direction shown by an arrow 224 in FIG. 17. Current flow in this direction produces armature rotation of the carriage motor 32 which moves the carriage in a direction toward the limit switch 61.

When the carriage reaches the limit switch 61, it closes its contacts to complete a circuit from the power supply 180 through the conductor 181, the conductor 211, the limit switches 60 and 61, the winding 195w of the reversing relay 195 and the conductor 182, so that the winding 195w is energized and operates the contacts of the relay. Contacts 195a and 195d are opened, and contacts 195b, 195c and 195e are closed. Current now flows through the conductor 181, the contact 186e, the conductor 201, the contact 195c, the carriage motor 32, the conductor 192, the contact 195b, the contact 186f, and the conductor 182 to the power supply 180. Current flow is now in a direction opposite that shown by the arrow 224, and the direction of rotation of the armature in the carriage motor 32 and, accordingly, the direction of motion of the carriage 31, is reversed. when the carrige moves away from the limit switch 61, the switch is again opened. However, the contact 195e connected in parallel with the limit switch 61 provides a holding circuit keeping the winding 195w energized after the limit switch 61 has been opened.

At the other end of its travel, the carriage strikes the normally closed limit switch 60, causing its contacts to open. This breaks the circuit energizing the winding 195w, and the relay returns to its normal configuration with the contacts 195a and 195d closed and the contacts 195b, 195c and 195e opened. Current flow through the carriage motor 32 again resumes in the direction shown by the arrow 224, and the direction of motion of the carriage reverses. When the carriage leaves the limit switch 60, its contacts again close. However, because the contact 195e and the limit switch 61 are both open, the winding 195w remains deenergized.

The saw blade 11 is thus reciprocated or oscillated with the carriage 31 beneath the sensor 22 by the motor 32, while it is rotated by the motor 35. Should a defect or improperly tensioned portion of the saw blade come beneath the sensor 22, this defect is detected and the sensor causes the signal control module 220 to energize the winding 214w of the sensor relay 214. When this occurs, the contact 214a is opened and the contact 214b is closed.

The opening of the contact 214a breaks the circuit energizing the winding 186w, so that the contacts of the relay 186 return to their normal conditions. Contacts 186a, b, e and f open so that operating voltage is removed from the motors 32 and 35. Contacts 186c and d close, connecting the resistor 191 across the armature of the saw blade drive motor 35. As will be readily understood by those skilled in the art, the placement of this load across the motor armature serves as a brake, swiftly stopping the motor 35. Contacts 186g and h place the resistor 200 across the armature of the carriage motor 32, so that this motor is also quickly stopped. The motion of the saw blade is thus arrested promptly. It should be readily apparent that the resistor 200 will serve its braking function regardless of the condition of the relay 195, so that the resistor may be used to stop the motor 32 in either direction of operation.

The closing of the contact 214b of the sensor relay 214 energizes the winding 205w of the time delay relay 205 through the conductor 181, the sensor drive switch 167 via the terminal 167a, the contact 214b, the conductor 215, and the conductor 182. This closes the contacts 205a and 205b and opens the contact 205c. A time delay is provided in the relay 205 only upon returning the contacts to their normal positions, and not during that portion of relay operation just described.

The closing of the contacts 205a and 205b connects the sensor drive motor 169 across the power supply 180 so that it begins operation, while the opening of the contact 205c disconnects the resistor 209 from across its armature. The sensor drive motor 169 moves the sensor arm 160 away from the sensor drive switch 167 and bback to the retracted position of FIG. 9, releasing the switch so that contact is made with the terminal 167b instead of the terminal 167a. This causes the winding 205w to be energized through conductors 181, 215 and 182, independent of the contact 214b.

When the sensor arm 160 begins to retract, the sensor 22 is withdrawn from the area of the defect which it had sensed, so that its output signal terminates and the winding 214w of the sensor relay 214 is no longer energized by the control module 220. This causes the contact 214a to close and the contact 214b to open. It is possible for the retracting motion of the sensor 22 to permit the contact 214b to open before the sensor drive switch 167 has contacted the terminal 167b. Under these circumstances, the winding 205w would no longer be energized and the sensor drive motor 169 would become disconnected from the power supply 180. To prevent this, a time delay is built into the relay 205 such that the contacts 205a and 205b remain closed, and the contact 205c remains open, a sufficient time to permit the mechanical switching of the sensor drive switch 167 to complete the holding circuit of the relay 205 through the terminal 167b.

The sensor drive motor 169 continues to operate until the sensor arm 160 has completed a full oscillation to the retracted position of FIG. 9 and a return to the operating position of FIG. 8, in which it contacts the sensor drive switch 167 once again. This causes the switch to disengage the terminal 167b and again contact the terminal 167a. This deenergizes the winding 205w and, after a short time delay, opens the contacts 205a and 205b to remove operating voltage from the sensor drive motor 169, and closes the contact 205c to connect the resistor 209 across the armature to quickly stop the motor.

If, when the sensor returns to its operating position above the saw blade, it still detects the defect which previously caused it to produce an error signal, the winding 214w of the sensor relay 214 will again be energizd, so that the time delay relay 205 will be energized through the contact 214b to continue operation of the sensor drive motor 169. This will occur repeatedly until, upon the return of the sensor 22 to its operating position over the saw blade, that defect is no longer detected; but when this occurs, the resulting deenergization of the relays 214 and 205 terminates operation of the sensor drive motor 169, and energizes the winding 186w of the relay 186 through the contact 214a to renew operation of the carriage motor 32 and the saw blade drive motor 35.

As can be seen in FIg. 17, The electrical condition of the carriage direction-control relay 195 is independent of the relays and switches utilized to control the starting and stopping of the motors 32, 35 and 169. Therefore, the condition of the contacts of the reversing relay 195 will be the same when the carriage motor 32 resumes operation as it was when it stopped for the correction of a defect.

OPERATION OF THE MACHINE

Overall operation of the tensioning and straightening machine 30 will now be described. Before a saw blade 11 is mounted on the carriage 31, the relative positions of the various components of the machine must be adjusted to accommodate a saw blade of that particular diameter and thickness. If the center of a saw blade is always positioned substantially at the center of the carriage 31, then certain permanent adjustments may be made. The carriage 31 should be moved as far from the carriage motor 32 as it is desired to travel. At that point, the limit switch 60 may be permanently mounted to reverse the direction of travel of the carriage 31 in the manner previously described. With the carriage abutting the limit switch 60, the hammer 24 and anvil 25 are positioned so that the hammer may strike the saw very close to, but not at, its center, whose position is adjustably fixed by the center biasing means 15, including the positioning bar 100 carrying the stud 101.

The sensor 22 should be directly over the anvil 25 when it is in its operating position; this can be adjusted by locating the sensor drive switch mounting arm 166 so that the sensor arm 160 engages the sensor drive switch 167 when the sensor is aligned over the anvil. The foregoing adjustments are independent of the dimensions of any particular saw.

The center stud 101 of the center biasing means 15 controls the position of the center of the saw blade 11. Accordingly, it must be spaced a distance from the drive wheels 84 and 85 of the saw blade drive assembly 34 which will permit the drive wheels to engage the saw blade at some optimum distance from the edge of the saw. This distance differs from blade to blade, depending on such variables as whether the saw blade is toothed or gulleted. By loosening the threaded fasteners 99, the metal block 97 holding the positioning bar 100 of the center biasing means 15 in place can be loosened so that the positioning bar 100 may be moved in either direction to set the center stud 101 at the proper distance from the drive wheels 84 and 85. This can be done by linear measurement, or by actually placing a saw in position on the center stud 101. The threaded fasteners 99 should then be tightened.

By loosening the nuts 67 on the clamping bolts 66, the position of the whole saw blade drive assembly 34 may be shifted along the carriage. The saw blade drive assembly should be moved to a position which places the center stud 101 at its desired location at the center of the carriage 31. The nuts 67 are then tightened to lock the saw blade drive assembly 34 in position. The extra length of the drive shaft 105 permits this adjustment to be made without any need to move the saw blade drive motor 35.

Referring to FIGS. 12 and 13, the height of the lower drive wheel 84 may be adjusted by the spacer bolt 90 and draw bolt 91 so that the saw blade 11 rests on it in a position producing the desired blade curvature and permitting the blade to rest flat on the anvil 25 for proper hammering when the blade is released by the lift assembly 115. The spacer bolt 92 and nut 94 can then be adjusted so that the upper drive wheel 85 will properly grip a saw blade of specified thickness against the drive wheel 84, with a line between the centers of the two drive wheels perpendicular to the surface of the saw blade.

By loosening the clamping bolts 117 and nuts 120, the saw blade lift assembly 115 may be moved to any desired position, the only requirement being the positioning of the lift screws 136 at a suitable distance inward from the rim of the saw blade 11. This distance must take into account the curvature needed for proper tensioning and straightening of the particular saw blade, but can readily be determined by those skilled in the art. The positions of the lift screws 136 and their heights must be such that the sensor will properly track, that is, will remain at a fixed distance from, a correctly straightened and tensioned saw blade traversed under the sensor by the carriage 31. Testing may be accomplished by operating the machine with such a blade, omitting the use of the hammer 24, and reading the output of the sensor 22 through the use of a system of flashing lights or the deflection of a meter to determine how closely the surface of the saw blade is being tracked. The lift screws 136 are adjusted until satisfactory tracking is achieved. Proper adjustment can be reconfirmed at any time by this method, using as a standard a saw blade known to be properly tensioned and straightened.

When mounting a saw blade on the carriage 31, the sensor arm 160 should preferably be in the retracted position of FIG. 9, to prevent accidental damage to the sensor 22. Retraction of the sensor arm also actuates the air switch 172 to lower the lift screws 136 of the saw blade lift assembly 115 so that they do not interfere with blade mounting.

Loosening of the nut 94 of the saw blade drive assembly 34 lifts the upper drive wheel 85 and the center stud 101 so that the saw blade 11 may be placed in position. The nut 94 is then tightened as far as it will go; this is controlled by the previous adjustment of the spacer bolt 92.

With the saw blade thus secured in place, the carriage is moved to engage the limit switch 61, which is then positioned to set the limit of travel of the carriage in that direction. This determines the outer radial limit of the area of the saw blade which will be sensed, and must therefore be readjusted when blades of different diameters are to be treated.

The saw blade 11 is now properly mounted and operation of the tensioning and straightening machine may be begun by energizing the power supplies. The sensor arm 160 is moved from its retracted position by the sensor drive motor 169 to bring the sensor 22 to its operating position. The air switch 172 is actuated by the sensor arm, causing the lift screws 136 to dish the saw blade 11 and lift it from the anvil 25, as shown in FIG. 15. Continued motion of the sensor arm 160 brings it into engagement with the sensor drive switch 167, stopping operation of the sensor drive motor 169 and starting the carriage motor 32 and saw blade drive motor 35 as previously described.

The saw blade drive motor 35 causes the drive wheels 84 and 85 to rotate the saw blade 11 around the center stud 101 at a constant speed, as the carriage motor 32 reciprocates the carriage 31 between the limit switches 60 and 61. This combined motion produces a relative motion between the sensor 22 and the saw blade 11 such that the sensor traces a helical path over substantially the entire bowed surface of the saw blade, within the radial limits established by the positions of the limit switches.

The curvature of the bowed saw blade and the opposed curvature of the path of the carriage, shown by the arrow 51 in FIG. 10, combine to maintain the surface of a properly-tensioned saw blade at a substantially constant distance from the sensor 22. If at any point in the sensing operation a portion of the surface of the saw blade approaches closer to the proximity sensor 22 than the predetermined distance, this will be detected. The resulting signal produces the switching operation described in connection with FIG. 17, which immediately stops operation of the carriage motor 32 and the saw blade motor 35, promptly halting the saw blade with the sensed defect positioned over the anvil 25. Operation of the sensor drive motor 169 is begun by the sensor signal, and is maintained by the consequent release of the sensor drive switch 167 by the sensor arm 160. As the sensor arm 160 retracts outwardly, it releases the air switch 172 so that the new blade 11 is lowered onto the anvil 25. Upon reaching the limit of the retracting motion, the camming plate 174 on the sensor arm 160 engages the air switch 175, causing the hammer to sharply strike the defect in the saw blade.

The sensor arm 160 then returns toward its operating position over the saw blade 11, and the air switch 175 is released so that the hammer 24 is raised to its rest position. The sensor arm 160 again engages the air switch 172, which causes the saw blade to be lifted into its bowed configuration again. During the further interval of travel of the sensor arm 160, any vibrations in the saw blade 11 are damped out. The motion of the sensor arm continues until it re-engages the sensor drive switch 167. If the originally-sensed defect is still present, the sensor drive motor 169 will continue to operate and the hammering cycle will be repeated. When the defect is no longer present, the sensor drive motor stops operating when it engages the sensor drive switch 167, the carriage motor 32 and saw blade drive motor 35 begin operating again, and the sensing of the saw blade surface resumes.

When tensioning and straightening of one side of the saw blade has been completed, the sensor arm 160 is retracted from the saw blade to lower the lift scres 136, and the nut 94 is loosened so that the saw blade may be removed. The saw blade is then turned over and the process repeated. The saw blade should then be properly straightened and tensioned and ready for use. It may, however, be desirable with certain saws, such as highly defective ones, to operate on both surfaces of the blade two or three times, depending upon the extent of defectiveness and the degree of straightening which is desired.

THE MACHINE - SECOND EMBODIMENT

Figure 19:
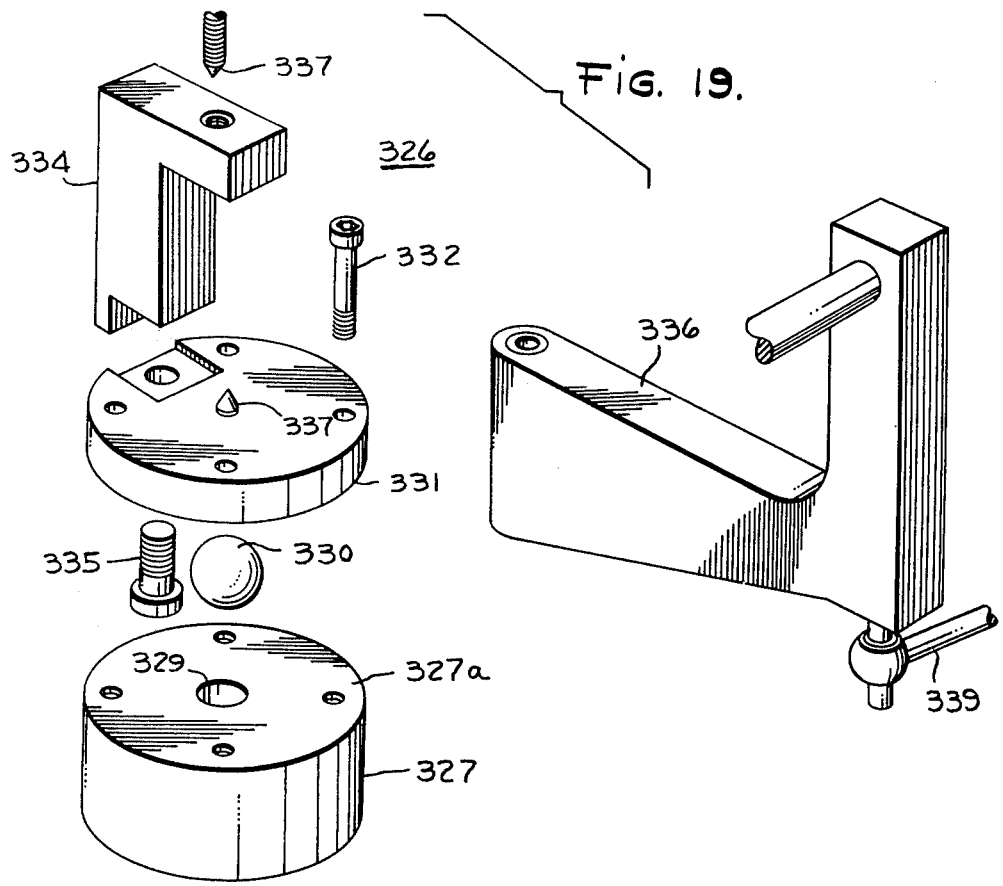
FIG. 19 is an exploded view in perspective of a sensor mount assembly of FIG. 18.

An alternative embodiment 300 of the tensioning and straightening machine for this invention is illustrated in FIGS. 18 and 19. This embodiment is exemplary of the use of movement of the sensor to aid in sweeping it over the blade surface. In the previously described embodiment, only the saw blade was moved during sensing, while the sensor remained stationary.

This embodiment of the tensioning and straightening machine 300 comprises a base 301 on which is mounted an oscillating table 302 driven by a motor (not shown), and includes limit switch means for reversing the direction of operation of the motor to produce limited arcuate movement of the table about a vertical axis, back and forth between the positions of the limit switches. The arc length of this oscillating movement does not exceed the radius of the saw blade to be treated, for reasons which will shortly appear.

In this embodiment a hammer 304, anvil 304 and sensor 306 are mounted on the table 302 for oscillatory movement therewith, while the center of the saw blade 307 is held fixed with respect to the base 301. As in the first embodiment, the saw blade is supported by a saw blade drive assembly 309, which is substantially identical to the drive assembly 34 of the first embodiment and is schematically represented in FIG. 18 by an upper drive wheel 310 and a lower drive wheel 311. Also supporting the saw blade 307 is a fixed saw blade lift assembly 312 having a pair of lift screws 314. Both the drive assembly 309 and the lift assembly 312 are mounted on the base 301 independent of the oscillating table 302. A center-biasing means 315 is also mounted on the base 301, and has a center stud 316 for locating and dishing the saw blade 307 in the manner previously described.

Figure 16:
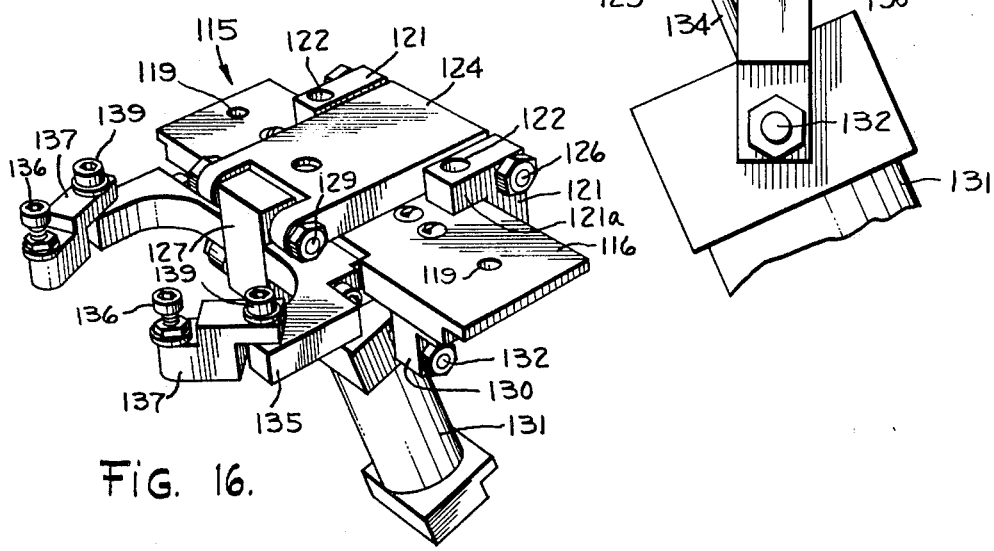
FIG. 16 is a view in perspective of the saw blade-deflecting means of FIGS. 14 and 15.

The lift assembly 312 is substantially similar in structure and operation to the lift assembly 115 of the embodiment illustrated in FIGS. 14–16, and is operated by an air actuator 317. The center-biasing means 315 is adjusted independently of the saw blade drive assembly 309, and is separately operated by an air actuator 319.

With the center of the saw blade 307 held in a fixed position with respect to the base 301 while the blade is rotated around the center stud 316, the preferred helical path of sweeping the sensor across the blade is attained by moving the sensor 306 itself. The anvil 305, hammer 304 and sensor 306 move together with respect to the saw blade 307, all being mounted on the oscillating table 302; the oscillating motion of these elements is in arcuate paths determined by their distance from the center of the table 302, and of an arc length determined by the locations of the aforementioned limit switch means. The anvil 305 is mounted on the table in a position beneath the sensor 306, and the hammer 304 is supported above the anvil by mounting legs 320 and a shaft 321. A striker block 322 is operable by an air cylinder 324 to strike a shaft 325 of the hammer 304 to impact it against the saw blade.

A sensor mount assembly 326 best shown in FIG. 19 comprises a base 327, which is positioned at the center of the oscillating table 302 but is fixedly mounted on the base 301 and does not turn with the table. A socket 329 is formed in the center of an uper surface 327a of the base 327 to accommodate a ball 330. A corresponding socket (not shown) is formed in the lower surface of an adjusting plate 331 to receive the ball 330. The adjusting plate 331 is attached to the base 327 by a plurality of screws 322 which may be, for example, four in number. The ball 330 is sufficiently large in relation to its sockets that it spaces the base 327 and adjusting plate 331 a predetermined distance apart when they are secured together by the screws 332.

A sensor arm mounting block 334 is secured to the adjusting plate 331 by a screw 335. A sensor arm assembly 336, to which is attached the sensor 306, is pivotally mounted on centering screws 337 between the adjusting plate 331 and the mounting block 334 so that the pivotal axis of the assembly 336 extends directly above the ball 330 which, in turn, is positioned at the center of the oscillating table 302.

A sensor drive rod 339 is connected between the sensor arm assembly 336 and a crank 340. The crank 340 is mounted on a sensor drive motor 341 for the purpose of moving the sensor with respect to the oscillating table 302, between a position retracted from the saw blade for hammering operations, and the operating or sensing position over the blade which is illustrated in the drawing.

The saw blade is rotated around the center stud 316 by the saw blade drive assembly 309. No lateral motion of the saw blade is provided for. The sensor 306, hammer 304, and anvil 305 are caused to oscillate over the surface of the blade by the motion of the motor-driven oscillating table 302, which moves back and forth arcuately between terminal positions established by the locations of a pair of limit switches (not shown), as previously described. These locations are adjusted so that the sensor sweeps back and forth between one terminal position close to the stud 316 at the center of the blade, and another near but radially inside the cutting edge and any gullets which may be provided in it. Because the sensor oscillates in an arc having a relatively large radius, substantially that of the table 302, its path approximates a linear radius of the saw blade.

The saw blade to be treated is bowed toward a predetermined curvature by an upward bias applied by the lower drive wheel 311 and the lift screws 314, in combination with a downward bias applied by the center stud 316. The structure of the sensor mount assembly 326 is such that the oscillating motion of the sensor 306 can be given the same curvature as the blade in planes parallel to the axis of rotation of the blade, i.e. normal to the surface of the undeflected blade, so that the sensor is maintained at a uniform distance from the locus of predetermined curvature of the bowed blade throughout its sweeping movements, and is therefore enabled to detect deviations of the blade surface from this ideal locus correctly. Since the base 327 is fixed in position with respect to the base 301, the adjusting plate 331 and sensor arm monting block 334 are also fixed in position. As the table 302 oscillates, the sensor drive rod 339, connected to the table through the now-stationary sensor drive motor 341 and crank 340, oscillates the sensor arm assembly 336 arcuately about an axis defined by the centering screws 337. If the centering screws 337 are vertically aligned with each other, the sensor 306 sweeps through an arc on which all points are at a constant distance from the table 302. However, by adjusting the screws 332, the adjusting plate 331 can be tilted over the ball 330 to form any of a variety of angles with the base 327. The arcuate motion of the sensor can thus be in a plane inclined to the table, with a result substantially similar to that provided by the tilted carriage 31 of the tensioning and straightening machine 30 previously described, i.e. that the sensor remains at a uniform distance from the locus of the curved plane or cylindrical segment in which the saw blade surface should ideally lie. In addition to providing for curved relative vertical motion, the two-directional adjustability of the adjusting plate 331 with respect to the ball 330 provides sufficient versatility of curvature to avoid any need for fine adjustment of the relative heights of the lift screws 314.

The hammer 304 and anvil 305 oscillate with the sensor 306 and the table 302, and so are always in position to hammer that part of the saw blade being sensed. Should a defect be detected, the motions of the oscillating table 302 and saw blade drive assembly 309 are stopped, the lift screws 314 are lowered from the blade 307, and the motor 341 is operated to retract the sensor 306 from its operating position above the defect. The defective area of the blade is then struck by the hammer 304. The sequence of operations may be controlled by suitable switches (not shown), operated for example by cams rotating with the crank 340.

VARIATIONS

Various modifications may readily be made; for example, the straightening and tensioning machine and method can be adapted for use on band saw blades.

The sensor 22 may be any of a number of known types capable of accurately detecting minute variations in the location of a small area of the blade, though I presently prefer to use a device which is responsive to variations in electromagnetic inductance across an air gap between the sensor and the blade. A photocell device responsive to reflectivity, or a mechanical feeler gauge, are subject to the possibility of inaccuracy caused by surface roughness or foreign matter on the blade surface. The same may be true of a pneumatic sensor responsive to a pressure drop through a gap between an orifice and the blade surface.

While the improved method has been described as it may be practiced in several automatic embodiments of my improved machine, it may also be practiced manually with the aid of appropriate equipment, including a fixture for supporting the blade and bowing it toward a predetermined curved surface, and a device for supporting a suitable sensor; these elements being relatively movable for sweeping the sensor over the blade surface, while maintaining a uniform distance between the sensor and the curved surface. In practicing the method manually it is not essential, although desirable, to maintain a hammer in alignment with the sensor, or to hammer each defect as it is detected before continuing the sensing, to eliminate the need for marking the locations of defects. Thus in its broader aspects, the method may include manual hammering. In applications requiring only a modest rate of production, this manual practice of the invention may be carried on by relatively unskilled persons, as it is only necessary to sweep the sensor over the surface, to mark the location of any defects which it may indicate, and then to hammer them, so that very little judgment is required.

In preferred embodiments and modes of practice of the invention, the saw blade is bowed elastically around an axis parallel to its diameter, to lie in a curved plane which is a segment of a cylinder that is not ordinarily of a circular cross section. However, the blade might be bent into the form of a segment of an oblate spheroid, such as an ellipsoid or the like; the sensor would then be swept through a parallel similarly-curved surface. In more general terms, it may be stated that the saw blade is elastically deflected toward the locus of a segment of the surface of any selected curved geometric solid having a predetermind contour, in which locus the blade surface would lie if the blade is correctly straightened and tensioned.

In the case where the sensor is physically moved to sweep the blade surface, as opposed to remaining stationary while the blade is physically moved, the sensor can then be swept through a segment of the locus of a second geometric solid which is congruent with, parallel to, and uniformly spaced from the first, thereby maintaining the sensor at a uniform distance from the desired locus of the blade surface. But in the case where the sensor is held stationary, the blade is physically moved in a manner to maintain all points of the locus of its ideal curvature at a uniform distance from the sensor.

The convex surface of the bowed saw blade may optionally be inspected for tight spots, which appear on this surface as areas that are flatter than the proper contour, by reversing the sensor to respond to surface areas that are farther from the sensor than the standard distance. However, it is more facile to sense the concave surface, as in the illustrated embodiments.

Another option is to use a sensor which responds to, and discriminates between, displacements by the hammer of the blade surface toward or away from the sensor. Situations may arise, such as when the impact is spread over an enlarged area by a worn hammer and anvil, the blade does not lie flat on the anvil, the blow is misaligned, or the blade is too thick for the weight and velocity given to the hammer, in which hammering may merely peen the surface and fail to permanently deform the blade clear through. Since peening spreads the surface, the result may be that the defect is raised rather than reduced. Detecting this occurrence permits immediate correction. In the case of a saw that is very thick, the opposite surface may be peened to offset this effect by relieving the stress, or the hammer may be given an appropriately-heavier mass or increased velocity.

I claim:

1. A machine for locating variations in tension in a saw blade, said machine comprising:
    carriage means constructed and arranged for mounting and elastically bowing a saw blade having a normally-planar major surface to deflect said surface toward the locus of a segment of the surface of a curved geometric solid having a specifically preselected contour, to which said blade surface would conform if the blade is properly tensioned and straightened;
    sensor means constructed and arranged for response to variations in its distance from the nearest area of said blade surface;
    and means constructed and arranged for supporting said sensor means and said carriage means for relative movement of said sensor means with respect to said curved locus at a predetermined substantially uniform distance therefrom;
    said sensor means being operatively connected to produce a signal only in response to a substantial variation in its distance from said blade surface occasioned by a local deviation of said blade surface from said curved locus.

2. A machine as recited in claim 1, together with selectively-operable motive means drivingly connected with said supporting means to produce said relative movement, and operatively connected for control by said sensor means to produce said relative movement in the absence of a signal from said sensor means, and to discontinue said relative movement upon production of a signal by said sensor means to permit corrective action to be taken immediately upon sensing of a local deviation of said blade surface from said curved locus.

3. A machine for locating variations in tension in a circular saw blade having a major axis, said machine comprising:
    carriage means constructed and arranged for mounting and elastically bowing a saw blade having a normally-planar major surface to deflect said surface toward the locus of a segment of the surface of a curved geometric solid having a specifically preselected contour, to which said blade surface would conform if the blade is properly tensioned and straightened;
    sensor means constructed and arranged for detecting local deviations of said blade surface from said locus only in a limited local area of the blade surface at a time;
    and means supporting said sensor means and said carriage means in operative relation for detection of said local deviations by said sensor means, said supporting means being constructed and arranged to support said carriage means and said sensor means for relative reciprocatory movement therebetween, and including means for rotating said saw blade about said major axis, to cause said sensor means to locate said local deviations in a larger area of said blade surface sequentially.

4. A machine as recited in claim 3, in which said supporting means are constructed and arranged to limit the relative reciprocatory movement between said carriage means and said sensor means, in a plane normal to said major axis of the saw blade, to a path length not exceeding the radius of the saw blade.

5. A machine as recited in claim 3, in which said supporting means are constructed and arranged: for relative reciprocation of said carriage means and said sensor means in directions having components both parallel to said normally-planar major surface of the mounted saw blade when undeflected, and normal thereto; and for controlling the latter component of relative reciprocation in direction and amount to maintain said sensor means at a uniform distance from said locus.

6. A machine as recited in claim 5, in which said supporting means comprise: a pair of parallel arms pivotally connected with said carriage; and means pivotally supporting said arms for angular movement of said carriage about parallel axes inclined to said normally-planar major surface of the mounted saw blade when undeflected.

7. A machine as recited in claim 5, in which said supporting means comprise: table means mounted for oscillatory movement about an axis normal to said normally-planar major surface of the mounted saw blade when undeflected; sensor-mounting means supporting said sensor means for oscillatory movement about an axis inclined to said major surface when undeflected; and means interconnecting said sensor-mounting means and said table means to produce oscillatory movement of said sensor means about said inclined axis as said table means is oscillated about said normal axis.

8. A machine as recited in claim 3, said supporting means positioning said sensor means at a uniform distance from said locus, said sensor means being responsive to deviations in the distance between said blade surface and said sensor means from said uniform distance.

9. A machine as recited in claim 8, said sensor means being responsive only to decreases in the distance between said blade surface and said sensor means to values less than said uniform distance, said deflected surface of the saw blade having a concave curvature, and said supporting means positioning said sensor means to confront said concave deflected surface for response to protrusions therefrom.

10. A method of locating variations in tension in a saw blade having a normally-planar surface, comprising the steps of elastically bowing the blade to cause said surface thereof to deflect toward the locus of a segment of the surface of a curved geometric solid having a specifically preselected contour, to which said blade surface would conform if the blade is properly tensioned and straightened;

selecting sensor means responsive to produce a signal only in response to a substantial variation in its distance from the nearest area of said blade surface;

and moving said sensor means relative to said curved locus at a predetermined substantially uniform distance therefrom, to detect local deviations of said blade surface from said curved locus.

11. A method as recited in claim 10, in which the step of relatively moving said sensor means is discontinued upon production of a signal thereby, to permit corrective action to be taken immediately upon sensing of a local deviation of said blade surface from said curved locus.

* * * * *

UNITED STATES PATENT AND TRADEMARK OFFICE
CERTIFICATE OF CORRECTION

PATENT NO. : 4,027,531
DATED : JUNE 7, 1977
INVENTOR(S) : CHESTER H. DAWSON

It is certified that error appears in the above-identified patent and that said Letters Patent are hereby corrected as shown below:

Col. 2, Line 5, "arua" should read as "aura": Col. 2, Line 23, "saws" should read as "saw" Col. 2, Line 24, after "are" insert --only--; Col. 2, Line 38, "wraping" should read as "warping"; Col. 4, Line 48, "by method" should read as "my method": Col. 4, Line 51, "resutls" should read as "results": Col. 4, Line 66, "exggerated" should read as "exaggerated": Col. 6, Line 45, "releive" should read as "relieve": Col. 7, Line 22, "The relative" should read as "This relative": Col. 8, Line 28, "effects" should read as "defects": Col. 10, Line 32 "bow blade" should read as "saw blade": Col. 10, Line 60, "60 and 61" should read as "60 or 61": Col. 11, Line 25, "pivot" should read as "pivotal": Col. 13, Line 8, "more" should read as "move": Col. 13, Line 12, "support" should read as "supporting": Col. 16, Line 22, "anvil 255" should read as "anvil 25": Col. 16, Line 43, "raw blade" should read as "saw blade": Col. 17, Line 9, "realy 186" should read as "relay 186": Col. 17, Line 34, "junction 106" should read as "junction 206": Col. 18, Line 22, "182. defect" should read as "182.": Col. 19, Line 13, "carrige" should read as "carriage"; Col. 20, Line 7, "bback" should read as "back": Col. 20, Line 46, "energizd" should read as "energized": Col. 23, Line 10, "new" should read as "saw": Col. 23, Line 28, "sensor" should read as "sensor's": Col. 23, Line 35, "scres" should read as "screws": Col. 23, Line 48, "for" should read as "of": Col. 23, Line 64, "anvil 304" should read as "anvil 305": Col. 24, Line 40, "uper surface" should read as "upper surface"; Col. 24, Line 45, "screws 322" should read as "screws 332": Col. 25, Line 30, "monting" should read as "mounting".

UNITED STATES PATENT OFFICE
CERTIFICATE OF CORRECTION

Patent No. 4,027,531                    Dated June 7, 1977

Inventor(s)    Chester H. Dawson

It is certified that error appears in the above-identified patent and that said Letters Patent are hereby corrected as shown below:

Column 26, line 51, "predetermind" should read as -- predetermined --.

Signed and Sealed this

Fourth Day of October 1977

[SEAL]

Attest:

RUTH C. MASON
*Attesting Officer*

LUTRELLE F. PARKER
*Acting Commissioner of Patents and Trademarks*